United States Patent [19]

Pizziconi et al.

[11] Patent Number: 4,832,034

[45] Date of Patent: May 23, 1989

[54] METHOD AND APPARATUS FOR WITHDRAWING, COLLECTING AND BIOSENSING CHEMICAL CONSTITUENTS FROM COMPLEX FLUIDS

[76] Inventors: Vincent B. Pizziconi, 3535 E. Highline Canal Rd., Phoenix, Ariz. 85040; Bruce C. Towe, 2331 S. Paseo Loma Cir., Mesa, Ariz. 85202

[21] Appl. No.: 36,353

[22] Filed: Apr. 9, 1987

[51] Int. Cl.[4] .............................................. A61B 5/02
[52] U.S. Cl. ...................................................... 128/632
[58] Field of Search ............... 128/632, 635, 768, 769, 128/630, 668, 669, 749, 750; 640/4, 27, 29, 35, 50, 51, 93, 118, 119

[56] References Cited

U.S. PATENT DOCUMENTS

| | | | |
|---|---|---|---|
| 3,572,315 | 5/1971 | Cullen | 128/632 |
| 3,983,864 | 10/1976 | Sielaff et al. | 128/632 |
| 4,221,567 | 9/1980 | Clark et al. | 128/635 |
| 4,265,249 | 5/1981 | Schindler et al. | 128/635 |
| 4,274,417 | 1/1981 | Delphy | 128/632 |
| 4,311,789 | 1/1982 | Nylen et al. | 435/10 |
| 4,340,615 | 7/1982 | Goodwin et al. | 128/635 |
| 4,388,166 | 6/1983 | Suzuki et al. | 204/403 |
| 4,415,666 | 11/1983 | D'Orazio et al. | 435/179 |
| 4,633,878 | 1/1987 | Bambardieri | 128/635 |
| 4,726,381 | 2/1988 | Jones | 128/632 |

OTHER PUBLICATIONS

"ASAIO 1987 Abstracts", vol. 16, Use of Capillary Filtrate . . . , May 1987.
"An Ultrafiltration Based Chemical Biosensor", Pizziani et al, 40th ACEMA, Sep. 1987.
"Biosensors in Artificial Organs", Am. Soc. Artifi. Organs, Guilbeau et al., Jul.-Sep. 1987.
"Use of a Capillary . . . Diabetics", Janle-Swain et al., Am. Soc. Artif. Intern. Organs, Jul.-Sep. 1987.

Primary Examiner—Max Hindenburg
Attorney, Agent, or Firm—Joseph D. Kennedy

[57] ABSTRACT

An anisotropic hollow fiber membrane is utilized to sample complex fluids for selected substances by convective flow of liquid and such substances, with conduct of the liquid to a sensor for analysis for such substances, to permit monitoring, particularly of body fluids, for such substances with short response times.

19 Claims, 10 Drawing Sheets

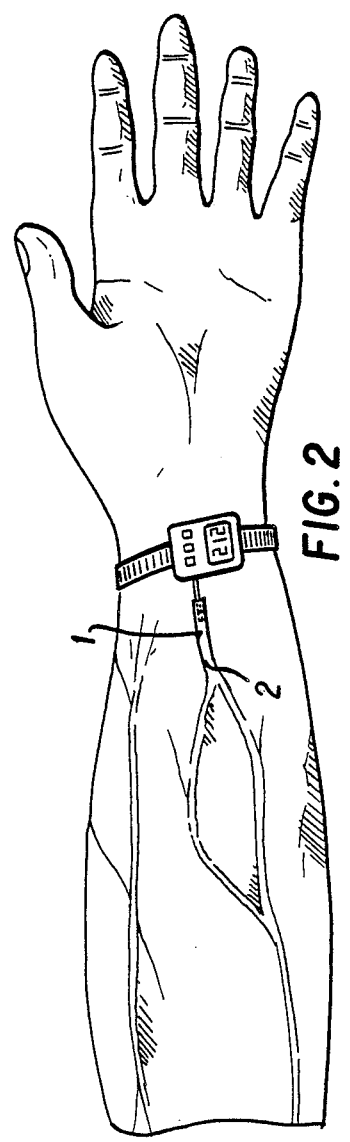
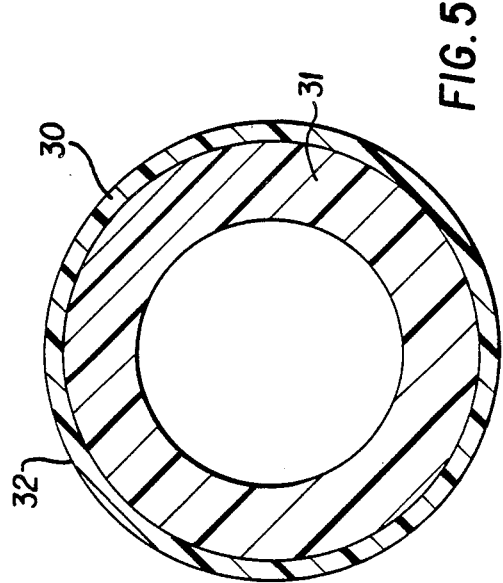

METHOD AND APPARATUS FOR WITHDRAWING, COLLECTING AND BIOSENSING CHEMICAL CONSTITUENTS FROM COMPLEX FLUIDS

FIELD OF INVENTION

This invention relates to a method and device for withdrawing selected fractions from complex fluids for purposes of collecting and measuring substances such as glucose. Use of this invention can be made wherever complex fluids are encountered and whenever chemical sensing, measuring, monitoring and control of selected substances is needed or is desirable. This invention is particularly useful for collecting and measuring selected substances contained in complex biological fluids such as body fluids.

BACKGROUND OF THE INVENTION

Laboratory instrumentation used in medicine and other chemically related industries has reached a high level of sophistication in recent years. For example, clinical laboratory instrumentation can now process hundreds of samples routinely in a day in batch modes, multiply and sequentially at a high sample rate, or selectively with specific test sets. Clinical laboratory methods of analysis fulfill much of the need for routine diagnosis; however, many clinical situations arise wherein the concentration of some chemical species change so rapidly that infrequent, intermittent measurements give the clinician a distorted evaluation of the patient status. In addition, this type of retrospective analysis does not reveal trends that might be considered significant and even dangerous.

Off-line or in vitro monitoring methods and apparati presently used are not capable of providing continuous measurement as they suffer from time-consuming laboratory analysis and other distinct disadvantages. For example, in animal or human medicine in vitro diagnostic instruments housing one or more sensing elements capable of measuring one or more selected substances in blood, urine and other body fluids have significant time lags (typically 20 minutes to one hour) between the time of sample withdrawal from the patient to when the sample is analyzed and the results made available. Thus, there is no instantaneous feedback or indications of trends which would allow the clinician better control over the administration of therapeutic agents and continually monitor their effects. In addition, repeated analysis or extended monitoring requiring more frequent or increased number of manual withdrawals of complex fluid samples poses other disadvantages to patient care; e.g., it increases the opportunity of air emboli or other unwanted substances to enter the body, consumes excessive volumes of precious body fluids, such as blood, and results in added expense for sampling supplies (disposable needles, syringes, collection tubes, reagents, etc.), technician time, and costly analyzing instruments.

Similar arguments teach against the use of off-line monitoring for industrial chemical process systems where any significant lag between the time a sample is withdrawn from a short-term or fast reacting process stream to when the sample is analyzed, would not afford the instantaneous assessment necessary in providing optimal control. Thus, time lags associated with off-line or in vitro analysis detract substantially from the use of this art when continuous or near-continuous analysis is desired and offer, at best, retrospective information.

The disadvantages and limitations associated with in vitro or off-line analysis have promoted considerable research toward the development of on-line sensing methods. For example, miniature sensors small enough to be used on or inside the body (e.g. intravascular) with the ability to continuously measure selected components in blood or other body fluids have been proposed based upon a wide variety of chemical transduction methods. These include sensing elements, such as, ion-selective electrodes (ISE) based upon potentiometric principles and more recently chemically sensitive field effect transistors (CHEMFETS) based upon microelectronic impedance-converting elements which are capable of measuring electrolytes, such as hydrogen, potassium, sodium, calcium and other ions. In addition, electroenzymatic based sensors utilizing polarographic principles, electrocatalytic sensing elements based upon direct catalytic oxidation, heat sensitive thermistor devices utilizing exothermic enzyme reactions, optical sensing elements utilizing fiber optic devices, CHEMFETS, ISFETS and other types of sensing elements have been proposed for the measurement of nonionic substances in complex fluids, such as dissolved gases (i.e.) oxygen, carbon dioxide), glucose and others.

The use of these proposed chemical sensors in the body is possible in a variety of ways, i.e., in vivo (transcutaneous, percutaneous, or implantable via subcutaneous, intravascular, intraperitoneal routes), and ex vivo (via extracorporeal circuits such as heart-lung bypass, kidney dialysis, hemoperfusion, apheresis and the like) modes, some of which allow access to the complete molecular spectrum of species in complex fluids in the body. In vivo and ex vivo chemical sensing modes hold the potential to continuously measure a wide variety of selected components in complex fluids, such as blood and the like, but have not overcome problems associated with the direct contact of the chemical sensor with the complex fluid. For example, major problems remain to be solved with long term implantable chemical sensors, including biocompatiblity problems with blood e.g. poisoning and/or fouling of the sensing components due to non-selective adsorption or precipitation, tissue encapsulation of the sensor, poor membrane selectivity and others all of which adversely affect sensor performance. Thus, in vivo implantable chemical sensors intended for continuous use are not yet satisfactory for routine patient care i.e. implantable chemical sensors would only be practical if they can remain stable for continuous and long term monitoring, and not require frequent recalibration due to sensor drift or replacement due to failure when exposed to complex fluids, such as blood. Furthermore, invasive chemical sensors employing sensitive electroactive materials or biologically labile components, such as an enzymes, are subject to deactivation when exposed to sterilization. Also, enzymes are known to perform suboptimally in complex fluids, such as, blood, where, in addition to the existence of antagonistic agents, limiting chemical reaction conditions exist which significantly reduce the activity or conversion capability of the enzyme. For example, it has been shown that when the enzyme glucose oxidase is employed to measure glucose in blood in vivo, the inherent limited oxygen environment in the body, where oxygen partial pressures are typically less than 100 mmHg, significantly reduces the activity level of the enzyme, thus restricting sensor performance in the absence of supplemental oxygen means. In view of the related problems associated with the direct contact of sensors with complex fluids, the packaging of sensors, i.e., design and location of the housing interfacing with the sensor, is critical for protection against environmental influences and is a major limiting factor in the design of biosensors. A more complete review of the current status and the limiting factors of chemical sensors can be found in I. Lauks, Symposium on Biosensors in Medicine, Medical Instrumentation, Vol. 19, No. 4., July-Aug, 1985; Engels et. al., Medical Application of Silicon Sensors, J. Phys. E: Sci: Instrum. Vol. 16. pages 987-994, 1983, and Potvin et. al., Proceedings of the Symposium on Biosensors, IEEE/NSF Symposium on Biosensors, Los Angeles, Sept. 15-17, 1984.

The present invention teaches the use of a filtration method and device for withdrawing, collecting and sensing chemical constituents from complex fluids and which overcomes many of the problems associated with continuous online sensing of complex fluids such as blood. It offers the capability of continuous measurement of dissolved species while selectively removing interfering substances prior to contacting the sensing element(s). It can be used in in vivo, implantable and percutaneous modes, as well as ex vivo with a wide variety of sensing elements. Its packaging offers a high degree of flexibility in the way and manner it interfaces with the sensing elements and the complex fluid, and in its ability to sense or measure species over a wide molecular spectrum simultaneously and without delay. It also allows the continuous collection of filtrate fractions of complex fluids which can be used, for example, for monitoring widely fluctuating body materials and for the measurement of substances existing at very low concentration levels. This contrasts with the prior art which generally teaches methods related to the chemical sensing of a relatively small number of only very low molecular weight species existing in complex fluids, such as, dissolved ions (eg. hydrogen, potassium), gases (eg. oxygen, carbon dioxide) and other relatively low molecular weight species (eg. glucose) and do not teach collection of filtrate fractions for chemical sensing. For example, use of the transcutaneous chemical sensing method is inherently limited to small diffusible gaseous substances, such as blood gases, which leave the complex fluid and permeate the underlying tissue and through the skin. Other proposed sensors which directly contact the complex fluid and utilize diffusive transport means to sense chemicals generally favor monitoring of low molecular weight, highly diffusible substances. Furthermore, the present invention does not require the use of anticoagulants as is generally required by the prior art that teaches percutaneous methods requiring whole blood withdrawal to measure components in the bloodstream.

Previous attempts to eliminate the necessity of withdrawing whole blood and the need for anticoagulants taught the use of a dialysis membrane barrier situated in a manner to isolate the sensor from directly contacting the complex fluid to prevent clotting, and more recently to improve selectivity, enhance sensor response, and/or reduce the exposure of sensing components to interfering substances (e.g. catalase, or peroxidase interference of glucose enzymatic chemical sensors). However, the use of diffusion limited membrane sensor devices, such as sensors utilizing dialysis membranes in a diffusive transport mode, restrict desirable sensor responses to only highly diffusible, low molecular weight species (e.g. blood gases, electrolytes, glucose) and suffer from the inherent inability to measure and collect larger molecular weight species in real time; and in addition, do not allow the simultaneous real time measurement and collection of both small and large molecular weight species coexisting in a complex fluid, independent of the capability of the sensing element(s) to measure larger molecular weight species while having an acceptable response time. This is because mass transport in a liquid medium based purely on diffusion with no convection in the same direction as the diffusion is a relatively slow random molecular process particularly as the solute molecular weight increases. Described by what are known as Fick's laws of diffusion, the diffusion flux, J, of solute i in its simplest form is given by the expression, $J_i = -AD (\Delta C_i/\Delta X)$, where A is area across which diffusion occurs, D is the diffusion coefficient of solute i, $C_i$ is the concentration of solute i and X is the distance. If a membrane, such as used in a dialysis process, is interposed between two fluid compartments having one complex and one simple fluid, the diffusive transport of solute i from a complex fluid such as blood across a thin dialysis membrane into an aqueous solution W in general is generally described as $J_i = A \{DH/l\}(C_B - C_W)$, where the quantity DH in the square bracket is called the solute membrane permeability, l is the distance, and the quantity $(C_B - C_W)$ is the concentration gradient of solute i that exist between the fluid compartments. As the diffusion coefficient decreases with increases in the molecular size or weight of the solute or analate, an inherent disadvantage of diffusion dependent membrane processes is that the solute membrane permeability, defined as the product of its solubility and diffusivity, decreases with increasing molecular weight. With typical dialysis membranes, this effect is significant having reductions of up to 50% or more in solute membrane permeability possible even with only modest increases in solute size. For example, permeability reductions of this magnitude as the solute size increased from 180 MW (glucose) to 1355 MW (vitamin $B_{12}$) were reported by Collins et. al., The Journal of Physical Chemistry, Vol. 83, No. 17, pages 2294-2301, 1979. In addition, as the difference in concentration of the solute between the two fluid compartments decreases due to diffusion so does the diffusive transport rate (flux) of solute decrease. Thus, the concentration response of an analate permeating into a fluid compartment opposite a complex fluid and separated by a dialysis membrane would typically be asymptotic in nature independent of its size, small or large, as it approaches the actual value in the complex fluid resulting in a longer sensor response time.

Unlike diffusion, a solvent volume flow occurs in membrane filtration where the total volume flux, $J_v$, is described by $J_v = L_p \cdot \Delta P$ where $L_p$ is the pressure filtration coefficient and also known as the solvent membrane permeability and $\Delta P$ is the hydrostatic pressure gradient and also known as the transmembrane presure (TMP). Thus in contrast to diffusion, solute transport by filtration means is determined primarily by the solvent filtration rate which in turn depends upon the solvent membrane permeability and the TMP. In general as the TMP increases, the solvent flow and the solute transport rate increases and is esentially independent of the solute size up to solute sizes where the rejection characteristics of the membrane become a factor. The solute retention characteristic of a membrane barrier is described by the reflection coefficient which is related to the solute sieving coefficient SC. The sieving coefficient, defined as one minus the reflection coefficient, is the coefficient for convective transport through the membrane and indicates the magnitude of the capacity for convective transport of the solute, with the bulk flow of solvent, across the membrane. In general, sieving coefficients of approximately one are possible over a much wider molecular weight range with filtration type membranes, such as ultrafiltration and microporous membranes, than with diffusion membranes such as dialysis. Thus, for a solute having little or no rejection ($R=0$) or a sieving coefficient of approximately one ($SC=1$), the solute transport rate is essentially the same as the membrane solvent filtration rate which in general increases as the hydrostatic pressure gradient increases and the solute filtrate concentration is essentially immediately equal in concentration to its concentration in the bulk fluid.

The present invention is thus intended to measure the concentration of selected substances in complex fluids, such as, blood, peritoneal, interstitial, lymph, cerebrospinal, tear, and other body fluids for purposes of medical research, diagnosis and treatment; as well as, in complex fluids used in biochemical engineering and biotechnology, such as, fermentation broths and the like for purposes of maintaining optimal control of chemical process fluid systems. Its capability of continuous measurement of one or more selected substances, small and large, in complex fluids offers additional advantages of interest to the clinical and biotechnology communities.

A particularly useful application of the present invention is the continuous measurement of one or more selected substances existing in body fluids, such as, blood. Such substances include dissolved gases, electrolytes, trace elements, simple sugars, such as glucose and other carbohydrates, drugs, triglycerides, lipids such as cholesterol, amino acids, nucleic acids, hormones such as insulin, enzymes, antibodies, complement and other proteins or protein derivatives and other biochemicals which range in molecular weight from less than 100 daltons to in excess of 100,000 daltons and even up to 1,000,000 daltons or so.

In clinical medicine, the present invention can afford the continuous monitoring of patient blood chemistries in a manner not yet possible or available with current technology. For example, in short-term critical care patient management, fast and accurate measurements of substances in whole blood are needed. The needs in critical care, intensive care, and emergency care are quite specific and well defined. They include determination of blood gases, pH, electrolytes($K+$, $CA++$, $Na+$), key metabolites (e.g., glucose, bilirubin, creatinine,), drugs of abuse (e.g., alcohol, cocaine, etc.), myocardial indicators including creatinine kinase-MD, lactate dehydrogenase, and determination of others is highly desirable. In long-term patient management the present invention can be used for continuous biosensing, in vivo, for the control of chronic disorders, such as, the metabolic disorder known as diabetes mellitus, as well as, for therapeutic drug monitoring, microbial substances, infectious disease detection, detection of cancer markers, monitoring of pregnancy and other hormone indicators, antigens and antibodies and their complexes which are characteristic of autoimmiune disease, for genetic probes, as well as, for ions, dissolved gases, key metabolites, such as urea, and others. In addition, with proper scaling the use of this invention for the on-line continuous monitoring of nutrients such as glucose is desirable in optimizing the product yield of genetically engineered substances from complex fluid mixtures used in chemical process biotechnology.

It is also apparent that the present invention can be used for monitoring local chemical events in the body. For example, it could be used to monitor the influence of a single organ on the composition of fluids by monitoring afferent and efferent blood vessels of body organs and the excreted and secreted products of these organs. The present invention can also be used to monitor the metabolic changes in an organ or the metabolic fate of substances such as drugs.

The prior art taught on-line or in vivo methods and apparati for the analysis of components in complex fluids over twenty-five years ago (see New York Academy of Sciences, Vol. 87 pp. 729–744, 1960), but they have experienced limited utility due to distinct disadvantages that these approaches fail to overcome when analyzing complex fluids, such as blood and the like. Furthermore, the prior art taught methods and apparati for the continuous measurement of substances in blood in vivo over twenty-five years ago, yet no practical and dependable device has come forth to meet this clear need; this attests to the unforeseen disadvantages and limitations that these devices suffer from and the clear need and advantages of the features offered by the present invention.

The disadvantage and limitations of cited teachings of the prior art will further illuminate more specifically the distinct advantages of the present invention. For example, it was as early as 1960 that Weller, et. al., and Ferrari et.al., Annals New York Academy of Sciences, Vol. 87, pages 658–669 and 729–745 respectively, (1960) and Kadish, Transactions of the American Society for Artificial Internal Organs, Volume 9, pages 363–367, (1963), disclosed an on-line continuous chemical analysis of blood glucose. However, these systems required the use of anticoagulants, such as heparin, utilized large, expensive and bulky equipment situated on a bench top located a distance from the patient, thereby requiring that excessive volumes of whole blood be pumped outside the body and discarde. In addition, these systems were able to measure only small molecular weight substances such as glucose, could not be used continuously for long-term monitoring purposes, had slow response times, and did not lend themselves to portability.

Another related disclosure, Coggeshall U.S. Pat. No. 3,785,772, teaches a device consisting of a pair of syringes which withdraw whole blood from a patient via venipucture, the addition of an anticoagulant to prevent blood clotting, a dialysis membrane to allow a diffusible species to be separated from the blood, a reactant which converts the diffusable species into a measurable reactant-blood constitutent complex and a sensor which can detect the concentration of the reactant-blood constitutent complex. However, the Coggeshall apparatus is also cumbersome, limited to intermittent analysis of only low molecular weight species, and requires excessive blood volumes for near continuous multiple sequential analysis. The reactant also needs replacement after each measurement as it forms an irreversible complex and is thus unable to sense instantaneous changes in the body.

Further improvements to these methods were made by the apparati of Clark et.al. in U.S. Pat. Nos. 3,838,682 and 3,910,256 which comprised an intermittent withdrawal and monitoring system for small molecular weight substances, i.e., blood gases, ($O_2$, $CO_2$) and pH. These patents disclose a system wherein whole blood is automatically and intermittently withdrawn from an arterial catheter and delivered to a fully automated blood gas analyzer measuring system for analysis and return to the patient. The main disadvantage of this system is its inherent limitation to intermittent withdrawal sampling frequency and analysis. Also, its excessive blood volume precludes continuous monitoring of blood constituents, and additional reagents and solutions are required to maintain sterility and patency of the catheter, A further disadvantage is its inability to measure other body fluid constitutents and its inherent nonambulatory nature.

These early attempts at the continuous measurements of constituents in whole blood were further improved upon by placement of various measuring devices in situ at various body locations either directly in contact with the complex fluid or separated by a diffusion controlled membrane barrier as a means of eliminating the necessity of removing whole blood from the patient. However, these disclosures in general were restricted to the measurement of only small molecular weight gaseous and liquid species, and did not easily lend themselves to continuous monitoring, and did not utilize convective filtration to obtain complex fluid fractions.

For example, Brumley, U.S. Pat. No. 3,123,066 taught the use of an optical catheter that could be inserted into a blood vessel and placed in direct contact with blood. However, this apparatus is inherently limited to selected optically sensitive species, such as oxygen, and did not teach methods to remove intefering substances. Rybak, U.S. Pat. No. 3,787,119 teaches the use of a multiple photometer for insertion directly into the bloodstream in direct contact with blood but is restricted to substances that can be detected by colorimetry and does not teach methods to remove intefering substances.

McKimley, U.S. Pat. No. 3,438,241 taught the use of a permeable membrane to selectively measure gases in gaseous and liquid mixtures. However, he did not teach the use of this apparatus for measurement of gaseous constituents in the body and for non-gaseous constituents in complex fluids in vitro or in vivo.

Polanyi, U.S. Pat. No. 3,461,856 combined the optical catheter taught by Brumley with a gas permeable membrane similar to that of McKimley for measuring the oxygen saturation of blood transcutaneously. However, this method irestricted to blood gas parameter measurements only. Other, more recent art reciting transcutaneous gas sensing of body fluids including Delpy U.S. Pat. No. 4,220,158 and Vesterager et.al. U.S. Pat. No. 4,274,418, have similar disadvantages and limitations.

Other prior art teaching invasive percutaneous methods of detecting substances in body fluids, although having potential access to essentially the complete molecular spectrum of dissolved species in body fluids, were inherently restricted to the sensing of small molecular weight gaseous species.

This included, Gardner et. al., The Journal of Thoracic and Cardiovascular Surgery, Vol. 62, No. 6, pages 844–850 (1971), which discloses a percutaneous method and apparatus to measure blood gases consisting of a diffusion controlled, gas permeable Teflon-coated cannula, whereby blood gases diffuse from tissue through the hydrophobic membrane cannula and are shown by a vacuum applied to the proximal end of the cannula to a mass spectrometer. This method is limited to sensing low molecular weight gases not to mention the expense, size and limited utility of a dedicated mass spectrometer for on-line blood chemistry.

Also, Seilaff et al, U.S. Pat. Nos. 3,983,864 and 4,016,864, teach a method and apparatus comprising a gas permeable membrane probe containing a carrier gas which is inserted into a blood containing vessel in the body. A carrier gas such as helium is then allowed to come into equilibrium with the blood gas via blood gas diffusion across the membrane into the carrier gas. The carrier gas is then removed from the probe for in vitro analysis. This device is also limited to gas analysis and hence limited utility for complex body fluid analysis, as well as, the inherent disadvantages associated with pure diffusional equilibrium processes and subsequent in vitro analysis.

Kowarski, U.S. Pat. Nos. 4,006,743 and 4,008,717 teaches a portable microdiffusion chamber for collection of widely fluctuating body materials. However, this device has many disadvantages including the requirement of whole blood withdrawal, the addition of anticoagulant, and limitations of diffusional collection means. It also requires off-line sensing and thus is not amenable to the fast response times for continuous on-line measurement.

Brantigan, U.S. Pat. No. 4,016,863 also teaches a percutaneous apparatus for in vivo sampling of blood gases in tissue consisting of a gas permeable membrane tube containing a liquid which is allowed to equilibrate with tissue gases. However, this method is restricted to discrete sampling since the gas permeable probe containing the equilibrated fluid must be retrieved from the body before blood gas analysis can be performed and it is also restricted to a narrow range of blood chemistry measurements i.e., blood gases.

A similar approach was reported by Myer et al, Surgery, Vol. 71, No. 1, pages 15–21 (1972), and Niinikoski et al, Vol. 71, No. 1pages 22–26 (197672), in which both methods teach the utilization of a gas permeable silicone probe filled with saline serving as the equilibration liquid which is allowed to equilibrate with surrounding tissue gases that diffuse across the gas permeable membrane probe into the saline solution and which is removed from the stationary implanted permeable tube for in vitro anaylsis. The inherent disadvantages are again its limited utility to monitoring gases only, its diffusional limited sampling period, multiple incisions and its intermittent in vitro analytical methodology.

Goodwin et al, U.S. Pat. No. 4,340,615 made further improvements to in vivo gas sensing by teaching the use of multiple membrane layer gas sensing probe to reduce problems of gas-depletion and flow dependence and improve response time. However, this art does not teach the measurement of non-gaseous species in complex fluids.

Other prior art taught methods of in vivo sensing of selected non-gaseous species such as glucose in complex fluids, such as blood. For example, Kadish, U.S. Pat. No. 3,512,517 teaches the use of an indwelling intravenous catheter having a dialysis membrane to measure blood glucose, in vivo. However, this apparatus requires the use of an anticoagulant and is limited to only highly diffusible, low molecular weight substances, such as glucose and cannot withdraw complex fluid fractions from whole blood.

Guilbault et. al., U.S. Pat. No. 3,948,745 teach the use of an amperometric electrode sensor housing immobilized enzyme held in contact with the sensing portion of the electrode by means of a cellophane dialysis membrane for the measurement of glucose. Again, this art does not teach how to withdraw complex fluid fractions from complex fluids such as blood nor does it teach in vivo sensing means. It is also restricted to highly diffusible low molecular weight components and is not suitable in its present form for long term continuous monitoring with a non-easily interchangeable enzyme component. Similar factors also pertain to Newman, U.S. Pat. No. 3,979,274.

Clark et al U.S. Pat. No. 4,221,567, teaches a percutaneous method and apparatus for the measurement of blood constituents in vivo which involve a permeable hollow fiber liquid-filled, diffusion-controlled, membrane probe which allows blood constituents, i.e., blood gases, to diffuse into the liquid contained in the probe which, after equilibration, is transported to sensors which are self-calibrating. The main disadvantages of this teaching are the inability to withdraw complex fluid fractions and sampling frequency limitations associated with diffusional processes, particularly as the molecular weight of the analate increases.

Merrill, U.S. Pat. No. 3,638,639, teaches a percutaneous apparatus for monitoring lipid-soluble blood constituents. Merrill discloses a system consisting of a catheter containing a membrane and a lipid solvent in which only lipids are allowed to cross the membrane by dissolution in the membrane whereupon they are dissolved in a lipid solvent and transported out of the body through a catheter for analysis. The major disadvantage of this art is its restriction to sensing only lipids.

Shimada et. al., U.S. Pat. No. 4,273,636 teaches a CHEMFET based sensor having a semipermeable membrane containing a light darkening dye or pigment. However, neither in vivo sensing nor withdrawal of complex fluid fractions by bulk convective filtration are taught. Also, a sensing means that directly contacts a membrane barrier would, for in vivo measurement, generally require implantation of both the sensing element and the membrane and thus restrict its utility.

Nylen et. al., U.S. Pat. No. 4,311,789 teaches the use of an extracorporeal dialyzer membrane means for measuring low molecular weight constituents in complex fluids such as glucose in blood. The main disadvantages are the complexity, size and nonportable nature of this apparatus, the fact that its diffusional transport basis restricts response times of higher molecular weight species, and its inability to sense in vivo.

Another percutaneous method and apparatus for the measurement of blood constituents in vivo is described by Schultz, U.S. Pat. No. 4,344,438 which teaches a dialysis membrane probe filled with a liquid containing receptor sites and competing ligands which cannot diffuse out of the permeable probe due to their large molecular weight and connected to a light carrying chamber in contact with a light source and detector. As selected plasma constituents diffuse across the permeable dialysis membrane, receptor site-competing ligand complexes are reversibly formed which affect the intensity of light emitted or absorbed in a way that is proportional to the concentration of the selected plasma constituents. The distinct disadvantages of this patent are the sampling frequency associated with diffusional and binding processes, the inability to withdraw and collect complex fluid fractions, the limitation on the number of constituents to be analyzed due to the finite number of specific binding agents and ligands contained in this implantable probe, and the requirement of an expensive and bulky fiber optic light source and detector.

Johnson, U.S. Pat. No. 4,356,074, teaches the use of a multilayer enzyme membrane sensor system to selectively exclude passage of high molecular weight interfering substances with one layer and other interfering low molecular weight substances with another membrane layer. However, this art does not teach methods of collection and sensing in vivo and relies upon diffusive transport of selected materials to the sensing element.

Suzuki et. al. U.S. Pat. No. 4,388,166 concerns an electrochemical measuring apparatus employing an enzyme electrode. The electrode is equipped with a filter membrane, an enzyme electrode, and an asymmetric semipermeable membrane over the immobilized enzyme membrane. The asymmetric semipermeable membrane in contact with a liquid with an organic ingredient to be measured, e.g. blood, serves to permit an ingredient such as glucose to contact the enzyme membrane while preventing contact with high molecular weight material which would contaminate the electrode. However, the patent does not utilize a bulk convective filtration means to transport the ingredient to the sensor but rather relies solely on diffusional transport of the ingredient through the asymmetric membrane barrier. Further, its use in this application is indicated to be not entirely understood but is suggested to suppress irregular diffusion and noise which interferes with the electrochemical apparatus of this art. It is also not concerned with procedures for in vivo sampling of body fluid components and does not utilize hollow fiber membranes.

D'Orazio et al, U.S. Pat. No, 4,415,666 teaches an enzyme electrode membrane apparatus in which the membrane has a thick porous layer dispersed with enzyme and a thin layer having a desired molecular weight cutoff of approximately 300 daltons. In its described form, this apparatus is limited to diffusional transport of selected species. It also does not teach bulk convective filtration means for collection and sensing and is not concerned with procedures for in vivo sampling of body fluid components and does not utilize hollow fiber membranes.

Bessman, et. al, U.S. Pat. No, 4,431,004 teaches a method and apparatus to account for oxygen limiting conditions that in general exist in glucose/glucose oxidase based sensors. This are teaches the use of a double electrode system whereby one electrode senses the absolute oxygen concentration. However, this art does not teach the use of a gas permeable membrane device to eliminate oxygen limiting conditions as is taught in the present invention.

Margules, U.S. Pat. No. 4,432,366 teaches a reference electrode catheter for in vivo sensing having a hydrogel membrane which forms an ion diffusion barrier between body fluids and sensor electrolyte material. The major limitation of this device is its sensing of only very small ionic species and it does not teach a bulk convective filtration means.

Cerami, et. al. U.S. Pat. No, 4,436,094 teaches a method wherein the sensor utilizes a semipermeable membrane probe containing a complexing agent that causes a change in the electronic activity of the sensor matrix rather than causing a change in the light emitted or absorbed. Specifically, the sensor is comprised of a semipermeable membrane housing an electrical charge transfer medium comprising a reversible complex of a binding macromolecular component and a charge bearing carbohydrate component, said membrane being permeable to glucose and other small molecular weight species and impermeable to the carbohydrate and macromolecular components. As glucose, present in the body fluid, diffuses across the membrane into the sensor fluid matrix, it displaces the charged carbohydrate with the result that the charged carbohydrate components enter the electric field and cause a change in the magnitude of electrical charge. Some of the disadvantages are similar to those of Schultz, and the procedure does not use an asymmetric hollow fiber ultrafiltration membrane to obtain complex fluid fractions as utilized in this present invention.

Other membrane sensor devices include Wilkens, U.S. Pat. No. 4,440,175 who teaches a membrane electrode for in vivo sensing of a non-ionic species such as glucose in which anion exchange material and a water-insoluble salt of the non-ionic species is dispersed in the membrane matrix; Peterson et. al., U.S. Pat. No. 4,476,870 who teaches a fiber optic oxygen in vivo gas sensing probe containing a hydrophobic gas permeable membrane envelope housing a fluorescent dye; Gough, U.S. Pat. No. 4,484,987, who teaches a sandwich-type membrane apparatus comprising both hydrophobic and hydrophilic membrane materials; Rogoff, U.S. Pat. No. 4,538,616 who teaches an implantable osmotic sensing membrane transducer for in vivo sensing of glucose; Lubbers, et. al, U.S. Pat. No. RE. 31,879 who teaches a fiber optic membrane probe for sensing gases in vivo, and Higgins, et. al., U.S. Pat. No. 4,545,382 who teach a ferrocine mediated enzyme sensor probe; and all of which fail to teach bulk convective filtration means for collecting filtrate fractions and sensing selected components in filtrate fractions obtained from complex fluid media.

SUMMARY OF THE INVENTION

The present invention is concerned with use of a semipermeable, hollow fiber membrane and particularly the use of an asymmetric and anisotropic hollow fiber membrane as a selective filter to remove portions of complex fluids, such as, body fluids for collection and analytical measurement. The invention involves contacting the complex fluid with the outer surface of an asymmetric hollow fiber membrane having porosity such that the solvent, i.e. water and desired analate in the fluid move convectively through the membrane to the fiber lumen, while some other fluid components, usually higher molecular weight or formed materials, are screened out by the membrane. The hollow fiber membrane employed has a relatively dense outer thin skin of porosity sufficient to pass the desired analate, and a generally less dense inner layer of greater porosity. This filter structure permits rapid filtration, quick response and good filtration stability. The permeation across the filter wall is by bulk flow of liquid induced by a pressure gradient, and it is a characteristic and a special advantage of the present invention that the concentration of desired analate in the filtrate liquid is essentially immediately proportional to the concentration of such analate component in the complex liquid. Therefore, the concentration of analate in the filtrate in the fiber lumen is a reliable indication of the concentration of such analate in the complex fluid. Since pressure filtration provides solvent flow together with solute transport across the membrane barrier, there is no need to provide a sweep fluid of diluent in the fiber lumen. Also, the present invention eliminates response time lags inherent in sensor methods relying on diffusive transport particularly as the molecular size of the analate increases. This allows real time measurement of steady state or equilibrium conditions of a wide variety of substances in complex fluids as analate in the filtrate as soon as a sufficient amount is present for the sensor. Since the porosity is such as to readily pass the analate, along with its solvent at solvent permeation rates, virtually instantaneous measurement of analate is possible. The invention is particularly concerned with measurement of components of body fluids, in vivo and ex vivo, as in inserting the hollow fiber membrane into a blood vessel to contact the flowing blood, or inserting it in an extracorporeal blood path. It is a particular feature of this invention that the filtration rates are responsive to pressure, making it feasible it many instances to obtain desireably short permeation and response times by increasing the transmembrane pressure gradient. Also, the present invention will be particularly suited for analysis for slowly diffusive, relatively high molecular weight components of complex fluids, e.g., molecular weights over 5000 or 10,000 or so, which are not amenable to analysis with reasonable response times by diffusion processes. Additionally, substances existing at very low concentrations may require collection of a substantial filtrate fraction for measurement to be possible.

A particular aspect of the invention is a device for sampling and analyzing body fluids comprising a hollow fiber of porous semipermeable anisotropic membrane with skin on the outside of pore size such that upon contact with body fluid it will permit the bulk convective flow of body fluid water and one or more desired analates to the fiber lumen, with provision for conducting material in the fiber lumen to a sensor for the analate.

It is an object of the invention to provide a method and device to determine the concentration of selected complex fluid constituents.

It is a further object of the invention to provide a method and device to determine the concentration of selected body fluid constituents.

It is a further object of the invention to provide a method and device to remove fractions of body fluids in vivo and ex vivo and to determine concentrations of particular analates therein.

It is a further object of the invention to provide a convective filtration membrane means to remove selective fractions of body fluids in vivo and ex vivo and to convectively transport separated fractions to sensor means.

It is still a further object of the invention to provide a method and device for sampling and sensing blood components which involves insertion of a very small diameter fiber probe into a blood vessel, quick response time and need for only a very small sample of blood components.

It is still a further object of the invention to provide a device for sampling and measuring blood components which is portable, relatively small and inexpensive, and which has relatively inexpensive and replaceable parts.

BRIEF DESCRIPTION OF THE DRAWINGS

FIG. 2 is a schematic illustration partially in section showing a wrist-watch size device with display on a human arm and connected to a blood vessel in the arm.

FIG. 5 is an illustration in section of the wall of an anisotropic fiber membrane.

FIG. 13 A is a 170x magnification of the end section of the polyamide fiber membrane showing the asymmetric nature of the membrane wall.

FIG. 14 A is a 100x magnification of the end section of the polyurethane fiber membrane showing the asymmetric nature of the membrane wall.

DETAILED DESCRIPTION OF THE INVENTION

Figure 1:
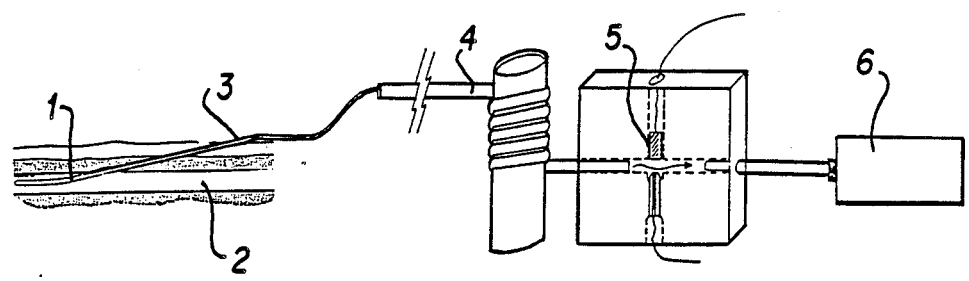
FIG. 1 is a schematic view of a device of the invention illustrating the hollow fiber membrane inserted in a blood vessel and connected by a tube though a glucose oxidase bed to a sensor and collection chamber.

The asymmetric semipermeable membrane used in the invention serves as a filter, permitting passage of the complex fluid liquids and material to be analyzed, but being essentially impervious to the bulk of materials of larger particle size which it is desired to exclude. In the case of analyzing substances in complex body fluids liquids, such as, glucose in blood, a membrane can be used which readily passes glucose (M. W. = 180 daltons) and other low molecular weight materials, but prevents passage of proteins and other high molecular weight materials. The membrane can be selected so as to exclude most materials of molecular weight over 5,000 daltons and still have sufficient porosity to pass glucose and other low molecular weight materials readily. If some somewhat higher molecular weight materials will not unduly interfere in the analysis, more porous membranes may be selected, so as to increase the solvent permeability and to be permeable to materials of molecular weights up to 20,000 or up to 50,000 or so, and it may often be desirable to permit passage of fairly high molecular weight material in order to improve filtration flow rates. Of course when it is desired to determine the concentration of one of the higher molecular weight materials, the membrane will be selected so as to be readily permeable to the desired analate, but will preferably still exclude some undesired materials of greater particle size. This can include the more homogeneous microporous membrane fiber structures having very large pores allowing passage of very high molecular weight marcomolecules but excluding cellular elements. Two or more membrane hollow fibers having differing permeation and transport properties may be used in combination to achieve desired selectivity and response time. Also, a multiplicity of membrane hollow fibers having similar permeation and transport properties can be used to achieve desired selectivity and response time.

The selectivity of a membrane depends to a great extent on its polymeric structure while the permeation rate is primarily a function of the solvent permeability coefficient of the membrane and the transmembrane pressure gradient. Typically, the permeation rate increases with the transmembrane pressure. Both the selectivity and permeation is controlled by the outer thin skin layer while the thicker underlying more porous structure acts as a support. Also, particular advantages relevant to stable and selective convective filtration can be utilized when employing a noningesting membrane material as taught in Dorson and Pizziconi et al, Transactions of the American Society for Artificial Internal Organs, Vol. 26, pages 155-160, 1978. The support walls of the fiber membranes used herein may for example be no more than 100 or 200 microns in thickness and often no greater than 50 microns. The thin outer skin of the membrane will desirably be relatively thin, as say no more than 5 microns and at times no greater than 1 or 2 microns. The fiber often will have an outer diameter no greater than 1,000 microns and sometimes less than 200 microns for body applications but could be substantially larger for other applications, such as, the monitoring of chemical process streams.

DETAILED DESCRIPTION OF EMBODIMENTS

A particular embodiment of the invention comprises a permeable hollow fiber probe sealed at one end, the open end of the probe being connected to a nonpermeable conduit that allows filtrate communication with chemical sensors and collection compartments. A preferred embodiment of the sensors and collection compartments is an externalized body surface compartment attached to the body, such as, a wristwatch-like device. The fiber probe material has a high solvent permeability that allows a substantial bulk filtrate flow rate and convective solute transport rate relative to any diffusive transport component.

A preferred embodiment of the invention for sensing and collecting low molecular weight complex fluid constituents, such as blood glucose, comprises a hollow fiber permeable probe having physical dimensions smaller than the desired body compartment. The diameter of a hollow fiber probe inserted into small arteries or veins would typically range from several microns to several hundred microns with the fiber probe wall thickness usually less than 100 microns. A guide wire or other semi-rigid member placed in the lumen of the fiber can be used to provide resilience and prevent potential kinking or collapse of the fiber and allows improved insertion capability. The hollow fiber should be constructed from materials having a relatively high and stable filtrate permeation rate but which reject larger molecular components, such as protein and formed elements, such as red blood cells. The fiber, for example, may be constructed of polymers such as polyamide or polyurethane or polysulfone with an asymmetric and anisotropic orientation of the polymer such that the polymer has a thin rejecting skin surface comprising the outer surface of the permeable probe contiguous with a more porous permeable substrate. A desirable feature of such a permeable material for sensing and collecting low molecular weight constituents is the ability to substantially reject high molecular weight components in a continuous fashion without substantially reducing the filtration capacity of the permeable probe. Ultrafiltration membranes have been characterized as non-ingesting, surface ingesting and protein transmitting as taught in Dorson, Pizziconi, et al, Trans. Am. Soc. Artif. Int. Organs, Vol. 24, Pages 155-160, 1978. Surface ingesting membranes result in reduced filtration performance when exposed to complex macromolecular fluid suspensions such as blood or plasma. Thus, an outer skin surface material, which does not substantially ingest higher molecular weight constituents such as blood proteins, will avoid impractical reductions in the filtrate permeation rate and unequal levels of the analate between the complex fluid and complex filtrate fraction, resulting from adverse sieving by ingested protein on the analate passing through the membrane, and is desirable. The substantially clear filtrate produced by the permeable probe described herein and residing in the probe lumen is withdrawn along the permeable tube lumen and into a conduit connecting the probe and the sensor component. The conduit may be made permeable or nonpermeable depending on circumstances related to the method of transduction of the sensing element. A preferred method of sensing and collecting is to withdraw the filtrate outside of the body before placing it in contact with the appropriate sensor(s). A sensor used in this manner for the measurement of glucose concentration can use well known polarographic techniques which measure substances which are directly related to glucose concentration. In this case, a typical sensor assembly could consist of an enzyme component such as glucose oxidase which is able to convert glucose to a stochiometrically related product such as hydrogen peroxide. The enzyme performance (activity) can be further improved by encasing it in a gas permeable conduit exposed to air to prevent oxygen depletion by allowing for oxygen to be continuously present as a means to enhance enzymatic conversion and prolong the life of the enzyme.

Gas permeable conduits can be made of hydrophobic polymers such as homogeneous or microporous membrane materials, such as, silicone and polyethylene, respectively. For example, small diameter and thin walled Silastic tubing made by Dow Corning was found to be a suitable homogeneous gas permeable conduit. Also, a filtrate pretreatment material such as activated carbon or resin can be placed before the enzyme cartridge to reduce any interfering substances. Further, a small collection chamber can be used for harvesting of filtrate fraction constituents. A preferred sensor and collection unit is a miniaturized compartment such as a wristwatch case which houses sensor pretreatment components, a flow-through sensor array, micropump, collection chambers and calibration materials.

The novel flow-through array described herein is particularly useful for convenient and miniaturized sensing. Thus, the filtrate from the fiber lumen passes through a very thin piece of gas permeable tubing packed with glucose oxidase enzyme immobilized on a silica carrier material. At this point near complete conversion of the glucose in the filtrate to hydrogen peroxide occurs by the catalytic action of the enzyme in a sustained oxygen environment. The proximal portion of the tubing contains a miniature platinum wire and silver chloride reference electrode. The amount of electric current flowing between the two electrodes is proportional to the hydrogen peroxide present. Various other electrical sensors for glucose are known to the art and can be used in the present invention; see U.S. Pat. Nos. to D'Orazio et. al. 4,415,666; Clemens et. al. 4,092,233; Clark 3,539,455; Newman 3,979,274; Suzuki et. al. 4,388,166; and Guilbault et. al. 3,948,745, the disclosures of all which are incorporated herein by reference. These patents in general involve use of membranes with electrodes, and it may at times be appropriate to dispense with one or more of the membranes when used with the hollow fiber membrane in accord with the present invention.

The complete device of the present invention is very simple, need contain no moving parts, and can be miniature in size. The complete sensor and all of the electronics needed for signal amplification and processing could fit into a small wrist-watch size package to be worn on a wrist band, with the fluid exit tip of the hollow fiber membrane exiting through the skin to attach to the package. Such a device would be inexpensive with replaceable and inexpensive parts. One of the problems with completely implantable devices for similar measurements is that critical components such as enzymes degrade or wear out and replacement requires removal and re-implantation. In the proposed wrist-watch location, the enzyme unit or the whole sensor can readily be replaced as necessary.

The present invention employs a hollow fiber asymmetric semipermeable membrane. The fiber has an outer semipermeable layer with very small pores over a thicker and very porous layer. The fiber can be of integral structure with a fine-pored relatively dense skin over a more porous support layer of the same material. Alternatively, the layers can be composed of different materials and one layer can be superimposed upon the other. The dual layer structure can also be formed by treating the surface of one of the layers, as in forming a porous hollow fiber membrane and then treating the external surface of the fiber with heat or by other physical or chemical treatments, or by coating or impregnating the surface with other materials to change the permeability of the surface. Regardless of the method of formation, the hollow fiber used is characterized by having a semipermeable outer skin which serves as a selective filter, permitting some materials to pass through largely by bulk convective flow, while other materials fail to pass through such skin and a more porous supporting layer which serves to support the outer skin but which may not contribute substantially to the selectivity of the filtering action and does not unduly increase the resistance to flow of the membrane. The pore size in the skin can vary, depending upon the material to be passed and excluded, but often will have pores mainly in the range of about 25 to about 200 angstroms and may even have pores ranging up to 5,000 angstroms or so. It has been found that an asymmetric membrane, as described, generally provides better filtration of complex fluids at desirable low hydraulic resistance than can be obtained employing a symmetrical hollow fiber membrane. However, any homogeneous membrane that is able to provide practical filtration rates may be utilized for this purpose.

In the present invention it has been found important to have the semipermeable skin be the surface in contact with the complex fluid. If the complex fluid is permitted to be in direct contact with the more porous support layer, rather than with the semipermeable skin, it has been found that the membrane is prone to plugging by the components and filtration rates are poor.

Figure 6:
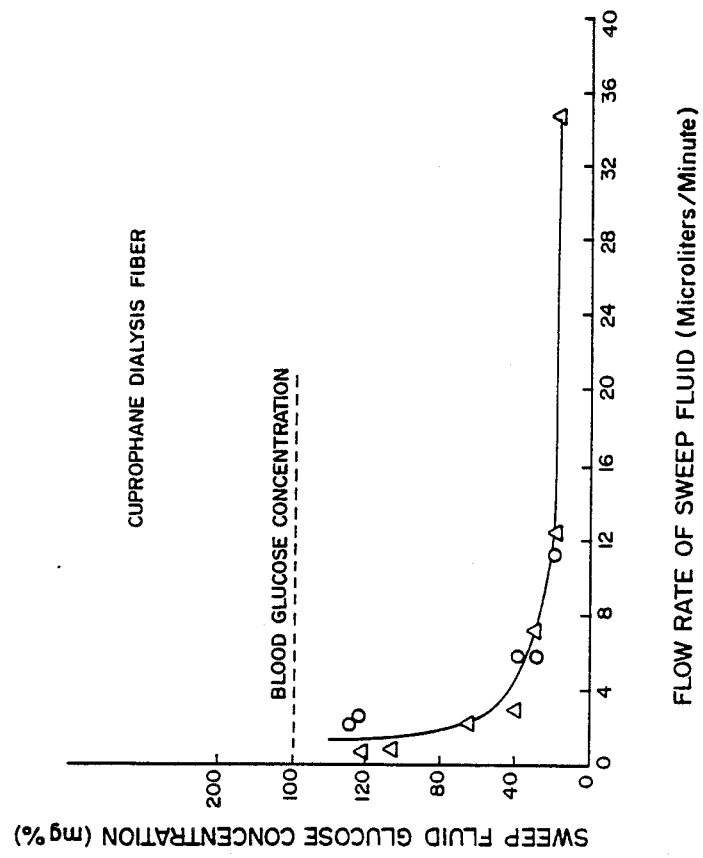
FIG. 6 is a graph showing the effect of sweep fluid flow rate on the diffusional membrane transport of glucose from the blood to an aqueous sweep fluid flowing through a dialysis hollow fiber lumen.

The present sampling process is not diffusional limited as is the case when using dialysis type membranes. In dialysis procedures the time required for a substance to diffuse across a membrane barrier from one fluid compartment to another fluid compartment and reach equilibrium is dependent on many factors including its diffusion coefficient, the composition of the fluid media, its membrane permeability, the thickness of the fluid and membrane films, the concentration gradient of the selected species existing between compartments, the dimensions of the compartments and the flow conditions of each compartment. From an order of magnitude estimate, the equilibration time ($t_d$) of a substance with a diffusion coefficient D diffusing across a stagnant film of thickness L is given as $t_d \simeq L^2/D$. It can be seen that longer equilibration times will occur with large fluid channels (including thicker membranes) and substances having small diffusion coefficients. In general, the diffusion coefficient decreases as the molecular size or weight of the solute increases. For example, the molecular diffusion coefficient decreases approximately by an order of magnitude in aqueous solutions as the solute molecular weight increase from 100 to 10,000 and would increase sensor response times by approximately a factor of ten for analates of this higher molecular weight. Also the diffusion coefficient for a given solute is in general lower in complex fluids, such as blood, than it is in simple aqueous solutions such as saline. In addition, the time to reach the true equilibrium value of a given solute can be significant under diffusion limited conditions especially if a non-zero (nonstagnant) sweep fluid flow condition is used. For example, even very low sweep fluid flow rates do not allow the true equilibrium value to be practically achievable even for small solutes such as glucose as shown in FIG. 6 unless the fiber lumen flow rate is extremely low or zero and/or the fiber length increased significantly. However, a near-zero or zero fiber sweep fluid flow rate would preclude locating the sensing element any significant distance (e.g. external to the body) from the body fluid compartment without increasing the sensor response time significantly. In any case, the sensing of the higher molecular weight solutes with lower diffusion coefficients using membranes under predominant diffusional transport mode would not be practical. In contrast, when ultrafiltration is involved the process is not diffusion limited and any desirable low or higher molecular weight substance in a complex fluid which can physically pass through the membrane unimpeded can be measured essentially in real time. This is because the response time is determined by the filtration rate of the membrane which is primarily dictated by the transmembrane pressure gradient, an independently controllable parameter and is not dependent upon the essentially self-limiting diffusion parameters mentioned previously. Thus, the membrane can be selected to give permeation rates for quick response, while still retaining desired selectivity. Anisotropic membrane probes having the desired convective filtration characteristics outlined above can provide permeation times such that quick sensor response times are obtainable for selected species over a broader molecular weight spectrum and most of the membranes employed will make feasible times less than 60 seconds, and even less than 30 seconds with actual values depending to a considerable extent on sensor volume. In contrast to membranes used in gas diffusion processes, the present membranes can be characterized as liquid permeable, particularly water permeable, although for desired selectivity membranes may be selected to prevent permeation of extremely high molecular weight liquid components. The transmembrane pressure can be deliberately increased to optimal flow rates and obtain desired short response times. In the body some fluids are under pressure above atmospheric, and vacuum can be pulled on the downstream end of the fiber, thereby making transmembrane pressures of hundreds of millimeters of mercury possible even in this environment. Thus the pressure in a particular case may be increased to 200 or even 300 or 400 mmHg or more in order to obtain flow rates for permeation and response times for sixty seconds or 30 seconds.

In the present invention the analate concentration in the filtrate in the fiber lumen can be considered as immediately the same as or essentially in equilibrium with that in the body fluid during convective filtration. This is because the analate permeates through the membrane along with the fluid water, and its concentration in such filtrate is relatively constant from the initial filtrate through further amounts of the filtrate. The analate concentration in the filtrate is essentially independent of the magnitude of the filtration rate and will only change in response to changes in the complex fluid. Thus the analate concentration in the filtrate is immediately representative of the concentration in the body fluid indepenent of the filtration rate. Since the movement of the fluid fractions is from the body fluid into the fiber lumen, the term "equilibrium" is not used here as meaning that a state has been reached in which movement from the fiber lumen is equal to that into the fiber lumen. The meaning is, rather, that the filtrate in the lumen is immediately representative of that in the body fluid and can be relied upon as a reliable measure of the equivalent concentration of analate in the body fluid. It will be noted that this differs from procedures in which the analate diffuses into fluid already present in the lumen, as in such procedures the concentration of the analate in the lumen will be lower than its counter part in the complex fluid and will change with time until equilibrium is reached in an asymptotic type fashion as its concentration gradient between fluid compartments approaches zero. In procedures in which a carrier fluid flows through the fiber lumen, it is thus difficult to reach the analates complex fluid concentration quick and often present problems in practice. Moreover, it involves balancing and controlling an additional flow stream. Thus, dilution with a potential loss of sensitivity is inherently a concern when a carrier fluid is used together with highly selective diffusion membranes often having low solute diffusion rates and providing only small amounts for sensing.

The filtrate in the lumen in the present invention is representative of that in the body fluid, particularly in respect to concentration of desired analate in body fluid water. However, it will be noted that the filtrate will not contain some of the high molecular weight materials or formed elements present in the body fluid, and the concentration of the filtrate will necessarily be different in this regard. Also the absence of the high molecular weight materials such as protein as well as well as cells will affect the numerical concentration of the analate in the filtrate on an overall weight or volume basis, but for a given membrane the concentration of a particular analate in the filtrate will vary from that in the body fluid by a relatively constant factor. For example, an anisotropic hollow fiber with an outer skin layer capable of transmitting dissolved components with molecular weight ranging up to 5,000 daltons and able to reject essentially all components greater than 5,000 daltons that is exposed to blood having a plasma glucose concentration of 1 mg/ml of whole plasma and a total protein concentration of 0.07 gm/ml of plasma water would represent an equivalent glucose concentration of approximately 0.932 mg/ml of plasma water in the filtrate since the volume of plasma water (VPW) is related to the plasma volume (PV) by the expression $VPW = PV(1 - TP/DP)$ where TP is the total protein concentration and DP is the density of the protein. The desired analate which moves physically across the membrane with the blood water or other liquid components, has largely the same ratio to such liquid components in the filtrate in the lumen, as it had to such liquid components in whole blood. In the present process the amount of material removed from the body fluid, e.g. a flowing blood stream, is usually very small, so the body fluid is not depleted with respect to any components and the concentrations are ordinarily not affected significantly and therefore the sampling and analysis are not affected. Glucose measurements can be obtained with removal of less than 1 c.c. of fluid.

In one application the present invention involves inserting the anistotropic hollow fiber membrane into a blood vessel, causing transportation of liquid and other blood components across the membrane to the fiber lumen and then to a sensing means for analysis. Such insertion into a blood vessel can be through a lumen of a catheter which has been inserted into the blood vessel, through a hollow needle which has been inserted in the blood vessel, or through a percutaneous skin access button, such as the Port-A-Cath made by Pharmacia, or the Hemasite made by Renal Systems or similar devices. If the catheter, needle, or skin button is left in place, the hollow fiber will generally exit the distal end of the catheter, needle, or skin access devices having direct contact with the flowing blood for a short distance. The end of the fiber in the blood vessel is plugged or capped or otherwise sealed, so that it is necessary for the blood components to be transported across the fiber membrane in order to enter the fiber lumen. Alternatively, a rigid rod-like member located inside the fiber lumen along its length with its distal end, coincident with the end of the hollow permeable fiber, forming a plug or seal with a sharpened end allows the hollow fiber apparatus to be used singularly as both a needle to penetrate the various tissue layers of the skin and blood vessel and as a filtration means for sensing and collecting desired substances in complex fluids. The filtrate in the fiber lumen is transported to a sensing means, which may be located at a proximal end of the hollow fiber, generally in an in vivo or ex vivo position. Alternatively, the hollow fiber may be connected to a semipermeable or non permeable conduit (relative to a liquid, gas or both) which can transport the filtrate to sensing means. It may be desirable to have the coupling with the non-permeable conduit at the skin of the subject or within the body to avoid possible changes of filtrate composition which may result from communication with other fluid compartments as the filtrate travels to the sensor. The transport of the filtrate can be assisted by applying either a positive pressure to the hollow fiber membrane or vacuum to the conduit, in communication with the hollow fiber membrane, as by means of a micropump generally located externally.

A particular embodiment of the fiber can have a hardened sharp plastic tip on its distal end to permit the fiber to penetrate tissue layers of the skin and blood vessel. Also a rigid or flexible rod-like member can be inserted in the fiber lumen to occupy a large part of the volume, thereby lessening the amount of filtrate volume needed to fill the lumen, and shortening response time. The invention is contemplated as useful while utilizing a single hollow fiber membrane to analyze for a single or a number of analates. However, it is also feasible to use two or more, or an array of fibers, probably with different permeabilities and suitabilitiy for passage and determinations of different analates, to analyze for a number of analates. In such a system, the various analate might be directed in controlled sequence to a single multi-purpose sensor, or directed to separate sensors.

If desired, the probe of the present invention can be used for sampling and measuring blood and other body fluids from artificial blood vessels and shunts implanted from one body location to another such as vascular grafts and hydrocephalus shunts or from extracorporeal fluid circuits such as those used for heart-lung bypass apparatus, artificial kidney fluid circuits, and the like. In former applications the probe will be used in essentially the same way as for sampling directly from a natural blood vessel in situ. The latter procedures involve transporting whole blood through conduits located outside the body allowing direct access to the complex fluid through a variety of sampling ports common to these systems or can be custom made to be an integral member of the fluid circuit. In any case, the possibility of clotting is substantially avoided in the fiber lumen and associated conduits as it involves the transport of non-clot activating lower molecular weight materials as filtrate through a fiber lumen. This advantage may be somewhat lessened when obtaining filtrate samples from peritoneal, cerebrospinal, lymph, tear and other body fluids but will in general allow substantially higher filtration rates to be achieved relative to filtration rates obtained with blood.

While a hollow fiber membrane can be inserted into a blood vessel and exposed to blood over the entire length of the fiber portion in the blood vessel, other embodiments are also suitable for use. Thus, the fiber membrane can be present as a sheath over a flexible tube which contains one or more apertures in its walls so that materials can filter through the fiber membrane and the apertures to reach the interior of the lumen. Alternatively, the hollow fiber membrane can be positioned in a cannula or catheter which has one or more apertures permitting contact of a body fluid through the apertures with all or a portion of the outer surface of the hollow fiber membrane.

The present invention makes feasible the miniaturization of a blood sampling and sensing device. The anisotropic semipermeable hollow fiber probe can be very small and its presence when used in body application should be well tolerated as a probe through the skin and into a blood or or other complex fluid vessel. In these applications, it can be made of known tissue compatible materials such as polyurethane. Since the fiber samples blood and other complex fluid materials primarily by ultrafiltration involving fluid convection through the fiber wall, the relative concentration of permeating components in the filtrate having a sieving coefficient of approximately one is essentially the same as in the complex fluid such as blood. The sampling therefore is very fast essentially dependent only on the magnitude of the transmembrane pressure for a given fiber and can be conducted in a continuous manner, providing a quick response to any changes of concentration of solutes in blood, or other complex fluids on the order of 30 to 60 seconds. The fiber lumen can be made very small such that its volume is less than a drop or less than a 10 microliters or so and therefore requires very little filtrate to provide liquid for flow to the sensing means. Also, sensing means are available which require only very small quantities for analysis, on the order of several microliters or less, about one-tenth of a drop. The fact that only very small quantities are needed for analysis makes it more feasible to use the probe on a continuous basis. Moreover, in the case where only low molecular weight materials such as glucose and blood water are sampled, fibrinogen and other clotting agents and cells will not cross the hollow fiber wall with the possibility of causing clotting or other problems. The use of heparin or other anti-clotting materials is not apt to be required in use of the present invention. In addition, it is advantageous to limit the removal of blood components from the system to the blood water and materials desired for analysis, rather than also removing formed elements such as red blood corpuscles and other important cellular blood components.

The monitoring of blood glucose levels is one of the applications of biosensors of great current interest to the medical community. Therefore much of the discussion and exemplification herein relate to determination of glucose levels. However, the present invention can also be utilized in determination of other substances in body fluids besides glucose. Analysis can be conducted for any other substances passing through the fiber wall with the fluid liquid components by analyzing the filtrate obtained at the outlet of the fiber. A sensor or other analytical means can be located ex vivo on the body within a few inches of the proximal end of the fiber filter membrane or placed in vivo such that it is adjacent to the fiber membrane when used in a percutaneous manner. Similarly, a sensor or other analytical means can be placed within a few inches or next to the fiber membrane which pentrates into the tube lumen of an extracorporeal perfusion circuit or a fluid compartment of a chemical process stream. This will be of particular interest for relatively low molecular weight substances for which concentrations are of interest for diagnostic or therapeutic purposes. For many such species very small sensors are available and would be introduced into the fiber outlet stream, for example such species as potassium, urea and blood pH. Other blood components which can be monitored include inorganic salts such as chlorides, carbonates, bicarbonates, sulfates, phosphates and iodides of sodium, calcium, magnesium, and iron; and ammonium salts, uric acid, amino acids, phospholipids and cholesterol; and gases such as oxygen, carbon dioxide and nitrogen. The hollow-fiber apparatus potentially is adaptable to a wide variety of sensing elements and its use can be expanded to include the sensing of other substances as new chemical sensing elements are developed. This could include sensors for myocardial indicators, drugs, hormones, enzymes proteins and protein derivatives, microbial substances, infectious disease agents, immune substances, genetic probes and other biochemicals.

Blood comprises a complex fluid matrix containing chemical substances. Permeable probes as used in the invention are capable of separating such complex fluids into simpler fractions. The separation involves a filtration process in which a portion of the fluid containing chemical substances moves through the semipermeable membrane barrier by bulk filtrate flow. The filtrate flow can be caused by a modest force differential, as by contact with blood at modest pressures above atmosphere on the outside and in the absence of liquid on the inside with the lumen having atmosphere or less pressure. The force can also involve application of a partial vacuum or evacuation of the fiber lumen by connecting the fiber to a micropump or other source of vacuum. In most cases, the pressure on the outside of the fiber must exceed the pressure in the fiber lumen for filtrate to enter into fiber lumen. The filtrate in the fiber lumen can be convectively transported through the fiber lumen for analysis at a sensor or sensors for one or more analates. It is not necessary to have any carrier fluid or diluent in the fiber upon contacting the complex fluid as the filtrate in the lumen includes liquid which can serve to transport the filtrate to a sensor for analysis. Since a carrier or diluent is not involved, the general permeation rate and time will not have much influence on the concentration of desired analate in the filtrate.

Since there is virtually instantaneous equilibration of desired analate in the filtrate and sampled fluid, and only very small amounts are needed for analysis, the present invention makes very quick results possible. It is appropriate for continuous monitoring, and for use in systems where administration of therapeutic agents is regulated in accordance with reading of particular components, as, for example, in administration of insulin to supply needs as determined by glucose levels. For example, the invention can be employed to sense in vivo changes in blood glucose values in a system wherein the amount and frequency of insulin injection from an implanted source is automatically regulated in response to such values. The present invention will be particularly useful in any situation where a prompt therapeutic action is indicated in response to particular blood component determinations. In use for monitoring blood components the present invention does not require removal of whole blood from the body. It rather generally involves only the removal of blood water and some low molecular weight analates, such as glucose or various ions, while higher molecular weight materials such as proteins and formed elements (cells) are retained in the blood. Since the materials removed are readily replaceable by normal metabolism, the sampling system of the present invention can be used for extended periods without undue loss of blood components.

In FIG. 1 an asymmetric hollow fiber membrane 1 lies within blood vessel 2 and is connected by impermeable connecting tube 3 to air permeable tube 4 containing immobilized glucose oxidase which tube is connectd to sensor 5 where hydrogen peroxide or oxygen, of both, can be measured, and then to waste or collection at 6. The hollow fiber membrane has walls of asymmetric structure (not illustrated) with a thin semipermeable skin on the outside and a more porous supporting interior layer.

FIG. 2 shows part of human arm in partial section with a wristwatch size snsor display with a hollow fiber 1 leading therefrom and inserted into a blood vessel 2 in the arm.

Figure 3:
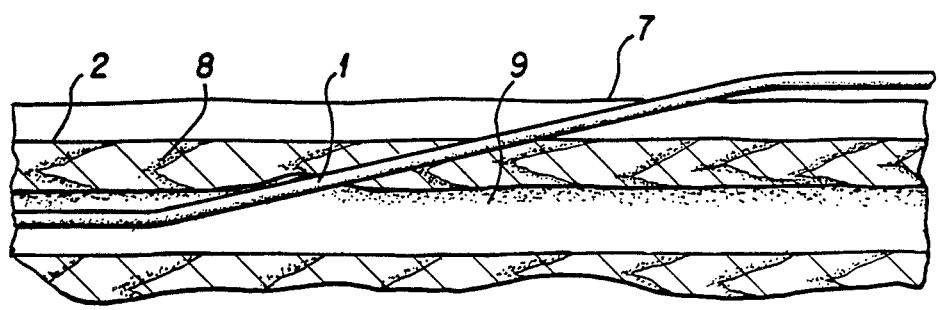
FIG. 3 is a sectional view of a fiber membrane penetrating into a body part and a blood vessel therein.

FIG. 3 is a sectional view of part of a body showing hollow fiber membrane 1 penetrating the skin 7 and wall 8 of blood vessel 2 to contact the blood 9 therein.

Figure 4:
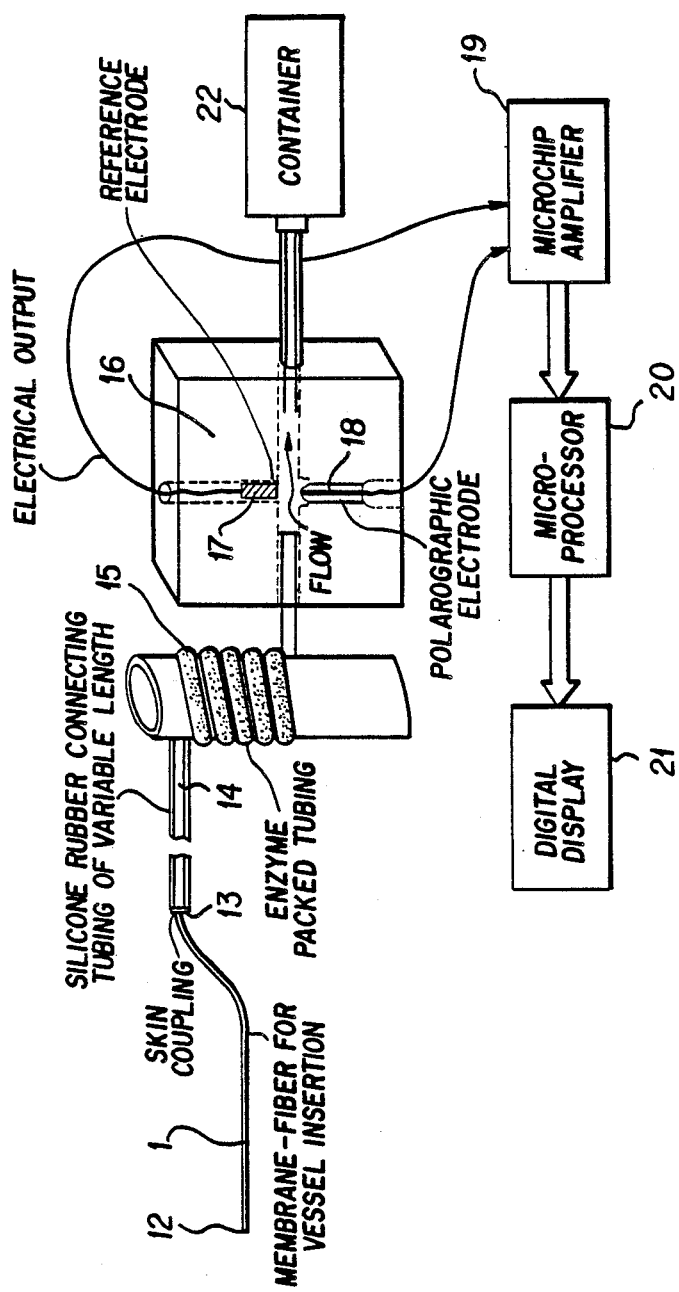
FIG. 4 is a schematic illustration of the parts of the sensor of FIG. 2, and its connection to a fiber membrane for vessel insertion.

FIG. 4 is a schematic drawing of a prototype sensor using the present invention, of the type generally illustrated in FIG. 2. In the device an asymmetric membrane hollow fiber 1 with closed end 12 is coupled at its other end 13 to a connecting tubing 14 which is connected at its other end to an enzyme packed tubing 15 which is attached to a support and then leads to an electrical cell 16 so that effluent from the tubing can contact a reference electrode 17 and a polarographic electrode 18. Leads from the electrodes are connected to a microchip amplifier 19 which is electrically connected to a microprocessor 20 and then to a digital display 21. Effluent is collected in container 22. In operation, a body fluid contacts the outside of hollow fiber membrane 1 causing liquid and desired analyte to permeate the fiber wall and flow through the fiber lumen and through connecting tubing 14 to enzyme packed tubing 15 where the analate, e.g. glucose, reacts under influence of the enzyme to generate a product, e.g. hydrogen peroxide from glucose, which is in the effluent from the enzyme packed tubing 15 which flows into cell 16 causing a current proportional to the hydrogen peroxide, which current is then amplified in microchip amplifier 19 and its relative quantity is displayed on digital display 21. The electrical current flowing between the electrodes is proportional to the amount of product, e.g. hydrogen peroxide, generated which in turn is proportional to the concentration of analate, e.g. glucose, entering the enzyme packed column. In a particular embodiment of the invention, the enzyme packed tube 15 is of material permeable to oxygen to provide an excess of oxygen for reaction of enzyme glucose analate. This avoids the possibility of error due to insufficient oxygen to react with all of the glucose present. The electrical output from the cell is amplified by a microchip and displayed using known technology. The display meter can readily be calibrated for concentration. The microprocessor 20, an optional component, will have the capability in programming to discard artifacts which may arise from non-uniformities in the filtrate flow through the sensor, from air bubbles and the like, to check the condition of the polargraphic electrode, and to automatically measure and compensate for temperature changes as well as provide other computational tasks.

FIG. 5 is an illustration in section of the wall of an asymmetric hollow fiber membrane. The membrane has a thin relatively dense layer 30 and a thicker less dense, more porous layer 31, which two layers form the composite structure of the wall. The thin layer 30, is the outer layer of the hollow fiber membrane, and its surface 32 is disposed to be in contact with body fluids when the hollow fiber membrane is inserted in a body cavity. The boundary between layers 30 and 31 may be distinct as shown or the layer may gradually merge into each other depending upon the procedure used for manufacturing the anisotropic hollow fiber.

EXAMPLE 1

As a comparison example, experiments using dialysis hollow fibers and a sweep fluid were conducted in order to compare results with those obtained in the present invention particularly in monitoring blood glucose concentrations in a flowing blood stream. The embodiment utilized cuprophane hollow fiber dialysis membranes having a homogeneous membrane structure and a nominal inside diameter of 200 microns with a nominal wall thickness of 11 microns. Cuprophane fibers were inserted into a flowing blood stream at approximately 37 C having a hematocrit of 47%, a total protein of 6.2 gm % and a glucose concentration of 158 mg %. The length of the fiber exposed to blood was approximately 2 cm. Dialysis experiment 1 used sterile water which was infused through the dialysis fiber lumen with a syringe pump at various flow rates ranging from 3.3 microliters/minute to 13.5 microliters/minute while samples were collected for analysis. Dialysis experiment 2 used phosphate buffered saline which was infused through the dialysis fiber lumen at flow rates ranging from 0.6 microliters/minute to 34.8 microliters/minute while samples were collected for analysis. The results of the two experiments are summarized in FIG. 6 which show a graph of blood glucose concentration in the sweep fluid as a function of the fiber sweep fluid (perfusate) flow rate.

Figure 7:
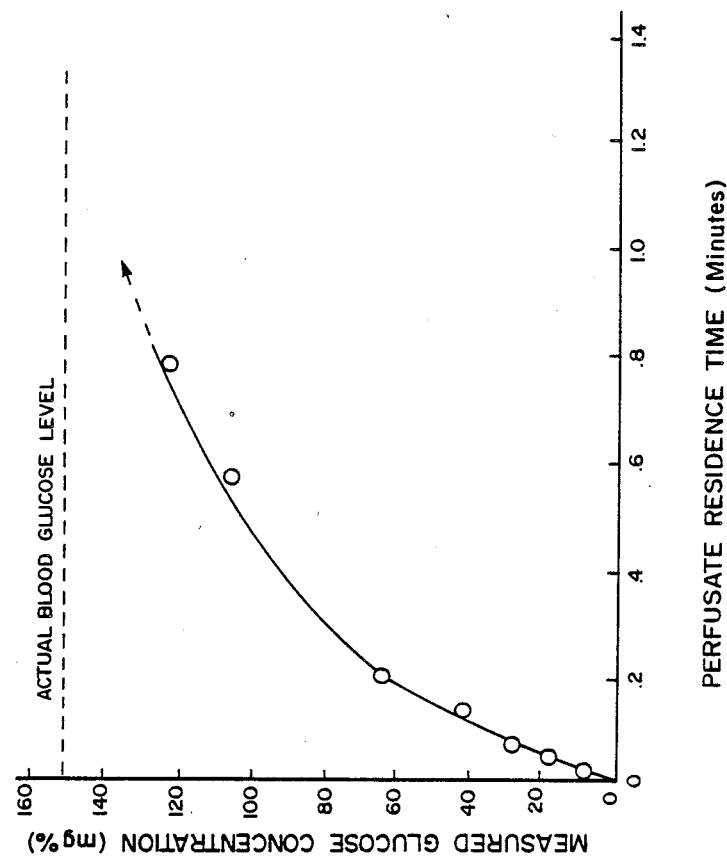
FIG. 7 is a graph showing the effect of the sweep fluid residence time on glucose concentration in the sweep fluid flowing in a dialysis fiber exposed to blood.

The small circles indicate values detemined in Experiment 1, while the small triangles indicate values from Experiment 2. As can be seen, equilibrium was not obtainable even at the lowest flow rate of 0.6 microliters/minute where only approximately 80% of the 158 mg % glucose concentration was reached indicating that longer residence times are needed to obtain true equilibrium values. The need for longer residence times is similarly shown in FIG. 7 based on the same data and plotting the glucose level in the sweep fluid versus the residence times of the sweep fluid. Even a residence time of about 0.8 minutes gives a sweep fluid concentration only slightly over 120 mg% glucose, well short of the actual glucose concentration. As the graft curve would be expected to approach the 160 mg % glucose level asymptotically, true equilibrium or close thereto would apparently be obtained only after a number of minutes whereas the attainment of exactly 100% of the actual equilibrium value may take significantly longer.

The apparent need for very low sweep fluid flow rates to achieve residence times necessary to attain equilibrium values of the analate result in inherently longer response times. This also restricts the sensor to be in very close proximity of the dialysis membrane. Similar considerations are apparent with longer dialysis fiber lengths.

EXAMPLE 2

Figure 8:
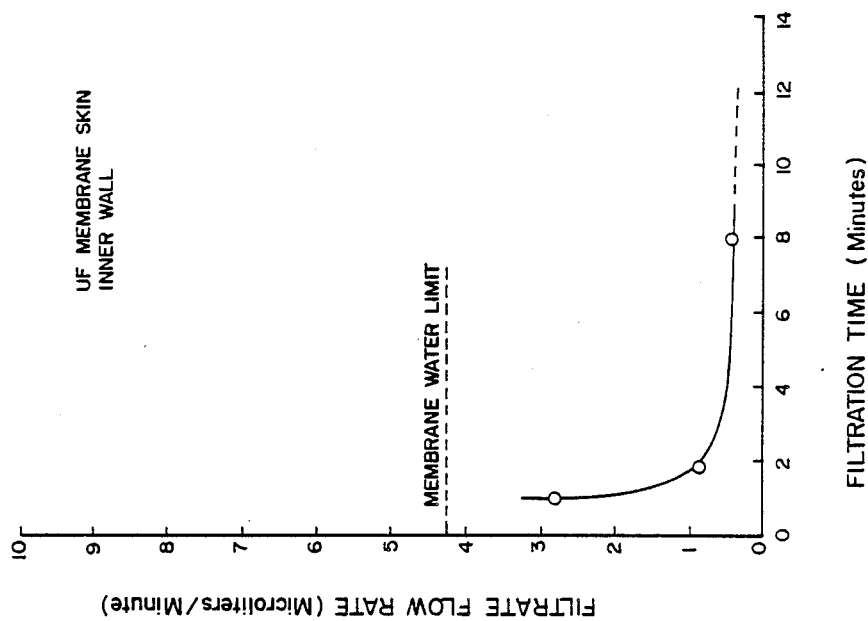
FIG. 8 is a graph showing the filtration response with time from an anisotropic hollow fiber membrane with a thin dense skin layer located in the inner surface of the fiber lumen and with the outer more porous membrane material exposed to blood.

An experiment was conducted to test the utility of an ultrafiltration anisotropic hollow fiber with an inner skin layer and outer more porous support membrane structure orientation as a sensor probe for the measurement of substances such as glucose in complex fluids such as blood. A single polysulfone ultrafiltration hollow fiber (Amicon Diafilter 30) having an inner diameter of approximately 200 microns and a wall thickness of approximately 70 microns, and an inner skin layer of approximately 2 microns with a membrane water permeability of 0.0425 microliters/minute/mmHg and an approximate 10 cm length of fiber was placed in an in vitro test apparatus at room temperature containing anticoagulated whole human blood with a glucose concentration of 102 mg % and a transmembrane pressure of 100 mm/Hg. The fiber blood filtration rate was approximately 2.8 microliters/minute but fell rapidly to 0.4 microliters/minute in less than ten minutes and asymptotically decayed to undesirably low levels within a short time thereafter as provided in FIG. 8. Thus, this experiment teaches against the use of anisotropic hollow fibers with an inner skin layer orientation as a sensing or collection means requiring practical and stable filtration rates. The membrane had an original water permeation rate of 4.25 microliters/minute at 100 mm Hg indicated as the membrane water line on FIG. 8.

EXAMPLE 3

Figure 13A:
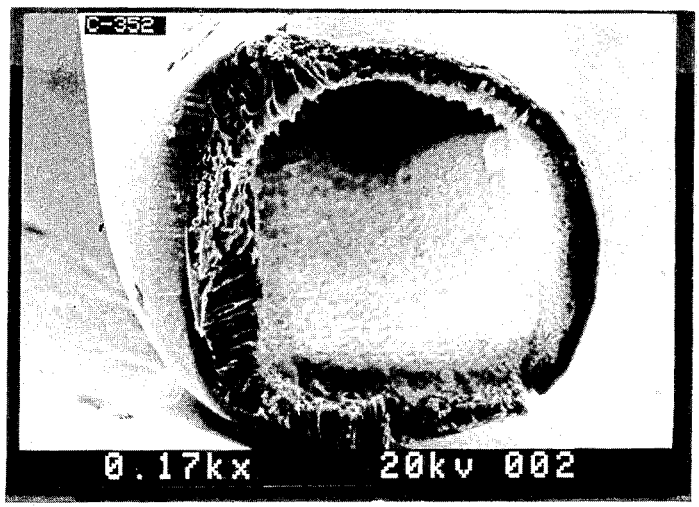
FIGS. 13 A, B and C are enlarged photographic views in end section of a polyamide fiber membrane with outer skin.
FIG. 13B is a 700x magnification of the same polyamide fiber showing the relative thick inner more porous suport layer and the relatively thin outer membrane layer.
FIG. 13C, at 1000x magnification, clearly shows the dense outer layer of the anisotropic polyamide membrane.
Figure 13B:
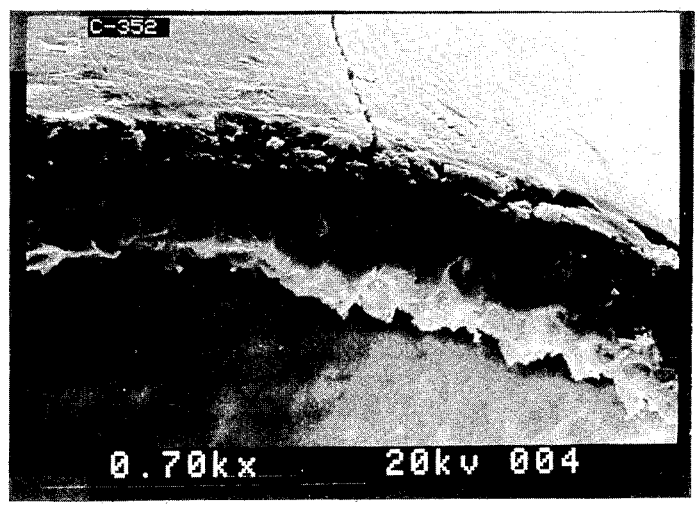
Figure 13C:
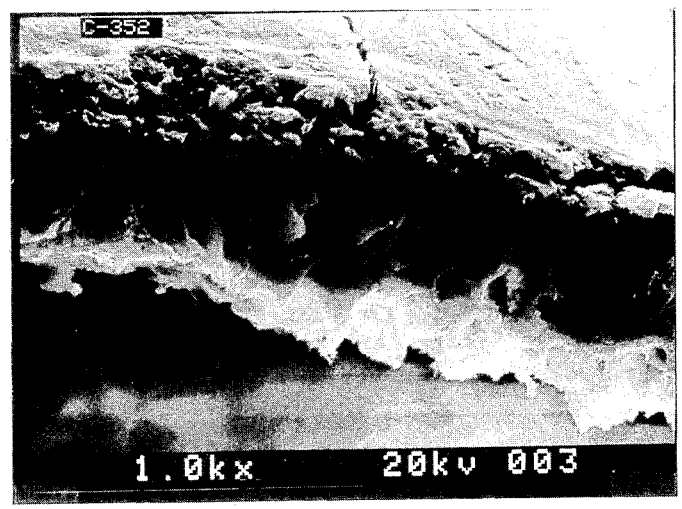

An embodiment of the filtration element of the present invention was demonstrated as useful in monitoring blood glucose concentrations. The embodiment utilized a polyamide polymer asymmetric hollow fiber having approximately a 95% rejection of myoglobin with an inside diameter of approximately 400 microns, a wall thickness of approximately 40 microns and an outer skin layer thickness of approximately 0.8 microns as shown in FIGS. 13A, 13B and 13C (base polyamide polymer of XU-218 formulation supplied by CIBA Geigy and polyamide hollow fibers from Reference No. 2882-22-C supplied by Amicon Corporation, 25 Hartwell Avenue, Lexington, MA.) The fiber was used to determine the complex fluid filtration characteristics of an anistropic ultrafiltration membrane with the skin layer on the outside.

Figure 9:
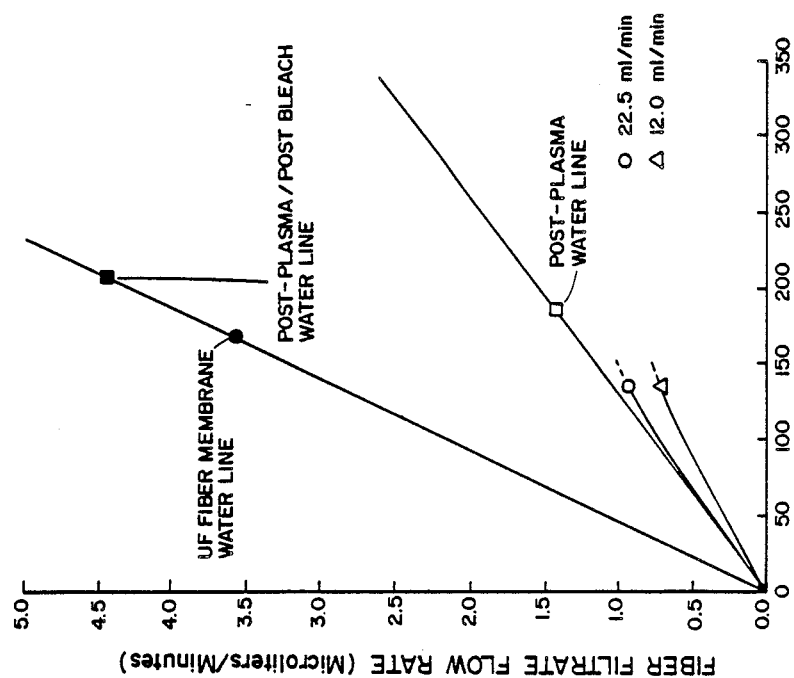
FIG. 9 is a graph showing the filtration response to transmembrane pressure imposed across an anisotropic ingesting-type hollow fiber membrane with a thin dense skin layer located on the outside surface of the hollow fiber and with the fiber outer surface exposed to blood.

After determining the water permeation characteristics, approximately 13.5 cm of the polyamide anisotropic hollow fiber was inserted in an in vitro recirculating test system containing human plasma at room temperature having a total protein concentration of approximately 8.1 gm %. The anisotropic fiber lumen was subjected to modest negative pressures of 100 mm Hg to 200 mm Hg. Plasma flow rates ranged from 12 ml/min to 22.5 ml/min. and results are shown for these two rates. The results shown on FIG. 9 indicate that stable and responsive filtration characteristics were achieved by the use of this hollow fiber asymmetric membrane with the skin on the outside. Furthermore, this experiment with filtrate flow rates proportional to transmembrane pressure shows that bulk convective filtration rates can be independently controlled by the transmembrane pressure and the complex fluid flow rate. Also, practical filtration rates were obtained relative to sensing element volume requirements of at least one microliter or more. However, it was noted that only partial recovery of initial water line was obtained after exposure to blood and indicated that this fiber was of the ingesting type and could only be recovered by applying a protein-dissolving bleach solution to the fiber. The water permeation rate ("water line") of the membrane, its maximum filtration potential, was determined prior to contact with plasma, as slightly over 3.5 microliters/minute, at about 160 mm Hg, using Sorenson's phosphate buffered solution. After the plasma contact experiment, the water permeation rate of the membrane was again determined, being somewhat less than 1.5 microliters/minute or less than 36% of the water filtration potential at about 185 mm Hg transmembrane pressure. After treatment of the membrane with bleach to remove protein, the water permeation rate was again determined, and fell on the same pressure/flow rate graph, i.e. water line, as the pre-plasma determination.

The same fiber was reused for filtration of fresh human blood having an hematocrit of 38 and a total protein of 6.95 gm %. The filtration response was similar to that obtained with plasma. The glucose filtrate composition of 86 mg % was essentially and immediately the same as the whole blood 88 mg % within experimental error.

EXAMPLE 4

Figure 10:
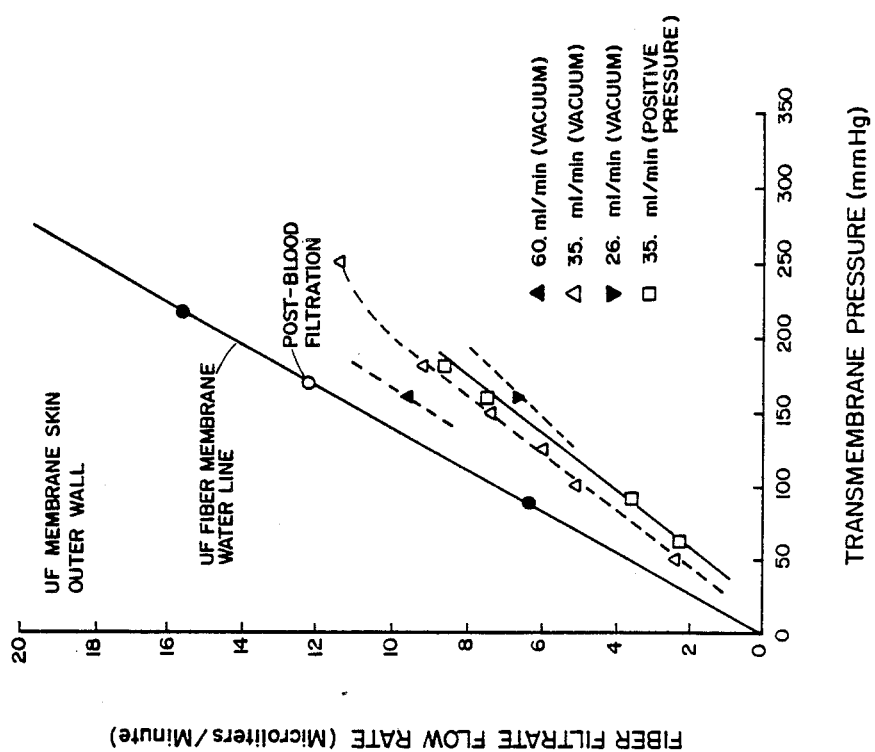
FIG. 10 is a graph showing the filtration response to transmembrane pressure imposed across an anisotropic noningesting-type hollow fiber membrane with a thin dense skin layer located on the outside surface of the hollow fiber and with the fiber outer surface exposed to blood.
Figure 14A:
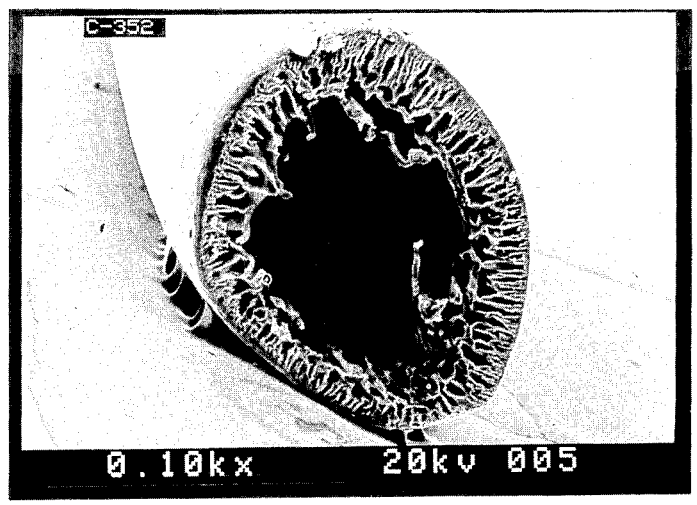
FIGS. 14 A, B, and C are enlarged photographic views in end section of a polyurethane fiber membrane with outer skin.
FIG. 14B and 14C magnified 170x and 350x, respectively, depict the relatively thick porous inner layer support structure contiguous with the outer, this and more dense membrane layer of the anisotropic polyurethane membrane.
Figure 14B:
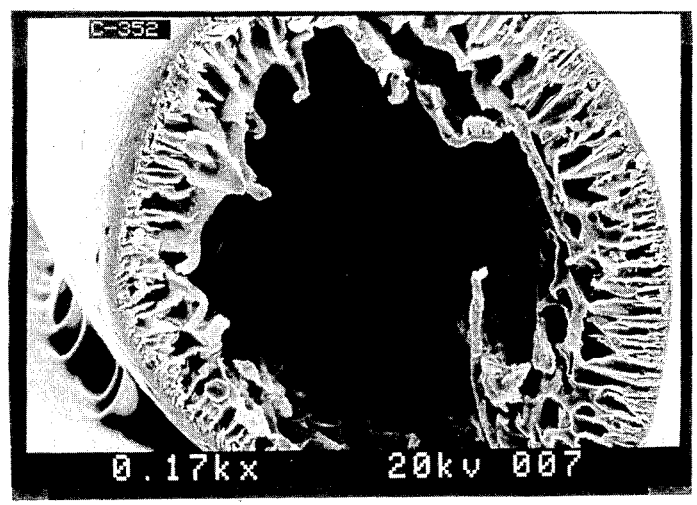
Figure 14C:
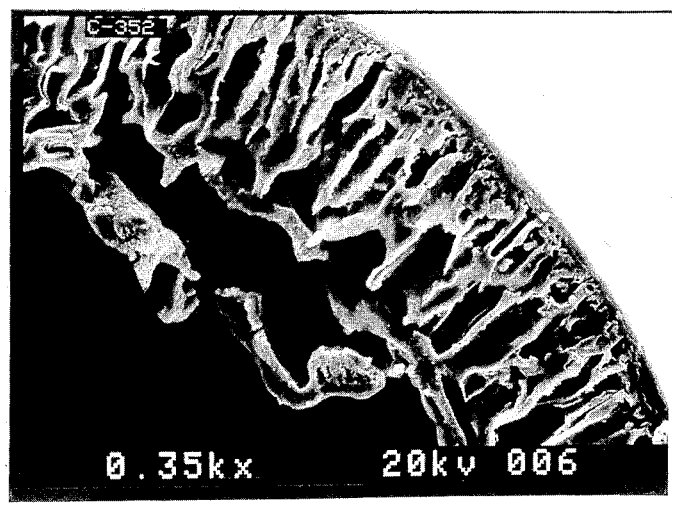

Another embodiment of the filtration element of the present invention was demonstrated in the experiment whereupon a noningesting anisotropic hollow fiber membrane manufactured from a copolymer containing a polyurethane having approximately an 80-90% rejection of bovine serum albumin (BSA), a 0.077 ml/min/mm Hg water filtration rate and approximately a 0.0264 ml/min/cm$^2$mm Hg water permeation coefficient (slope of water line) and a nominal inner diameter of 560 microns, a nominal wall thickness of 125 microns and an outer thin skin layer thickness of approximately 2.5 microns as shown in FIGS. 14A, 14B, and 14C (fibers made from a copolymer of polyvinyl chloride and polyacrylonitrile of approximate equal weight dissolved in a solvent containing an XM polyurethane polymer, Lot No. 2822-37, and supplied by Amicon Corporation, 25 Hartwell Avenue, Lexington, Ma.) Approximately 13.5 cm of anisotopic polyurethane fiber was inserted into the recirculating in vitro test circuit, as described in Example 3, containing whole human blood at room temperature having an hematocrit of approximately 36% and a total protein of approximately 6.65 gm%. FIG. 10 shows that the polyurethane fiber was of the noningesting type as the initial water premeation characteristics was essentially recovered post-blood filtration. Significantly higher filtration rates were obtained using a noningesting fiber ranging from greater than 2 microliter/minute to over 11 microliter/minute as the transmembrane pressure was increased; the filtration rates also increased moderately as the blood flow rate increased. A blood filtrate fraction volume in excess of 1,000 microliters was collected in approximately 5 hours of continuous filtration at these operating conditions. Graphs are shown for blood flow rates of 35.5 ml/minute (positive transmembrane pressure), 26.3, 35.5 and 60. ml/minute (partial vacuum). A fiber is considered non-ingesting if, after the contact with proteins or other macromolecules or cells under filtration conditions, its initial water permeation characteristics can be essentially recovered by aqueous washing procedures. It is advantageous to have a filtrate rate of two or more microliters/minute in order to provide a microliter of fluid for sensing in no more than 30 seconds, and preferably with operation at modest transmembrane pressures up to 250 mm Hg or so. The present invention involves convective flow of fluid through the membrane, and desirable membranes are characterized by fairly good water permeation coefficients generally in excess of 0.001 microliters/minute/mmHg/cm$^2$ and in most applications in excess of 0.01 microliters/minute/mmHg/cm$^2$ and may even up to 1.0 microliters/minute/mmHg/cm$^2$ or 10.0 microliters/minute/ mmHg/cm$^2$ or more.

EXAMPLE 5

Figure 11:
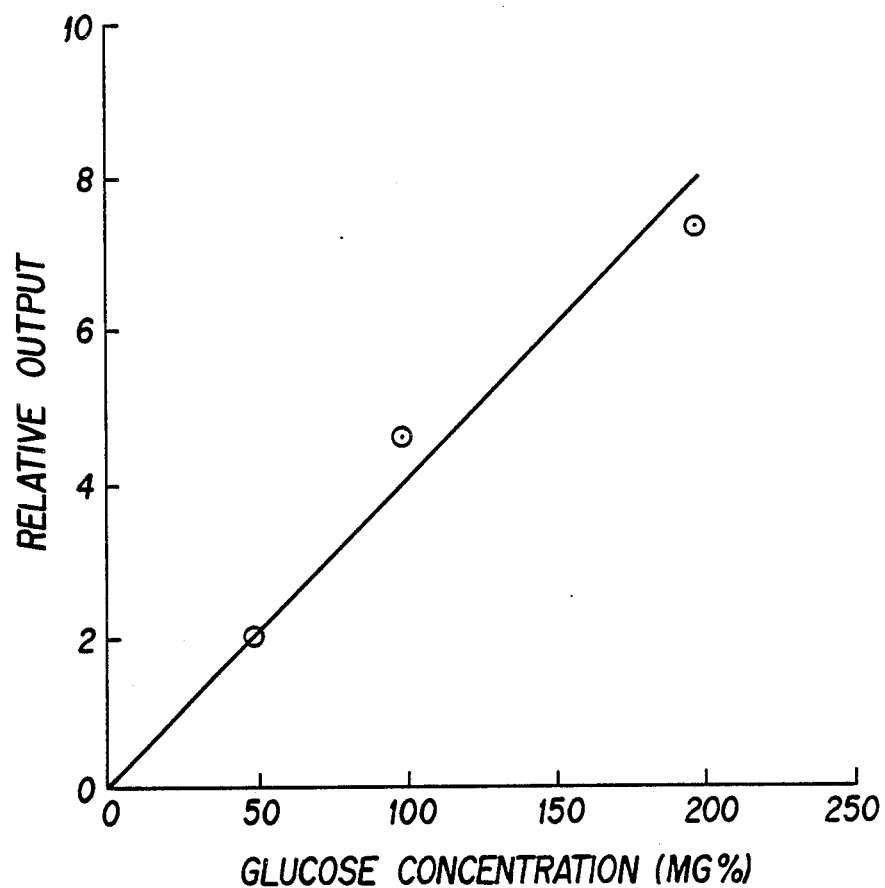
FIG. 11 is a graph showing the relative electrical output of the hollow fiber connected to a sensor, as a function of increasing glucose concentration in solution.

An embodiment of the present invention was demonstrated as useful in monitoring blood glucose concentrations. The embodiment utilized a polyurethane based asymmetric hollow fiber which was connected to an oxygen permeable Silastic tubing, 0.012 inches ID ×0.025 inches OD., packed with glucose oxidase enzyme (Product No. G8135 Sigma Chemical Co. obtained from Aspergillus niger of approximately 150 units/gram) immobilized on silica heads controlled pore glass beads, CPG, 400 mesh size, 440 angstrom pore size, supplied by Electronucleonics, Fairfield, N.J.), which led to a polarographic sensor able to measure hydrogen peroxide generated by the oxidation of the glucose by the enzyme glucose oxidase. The sensor had a platinum polarographic electrode and a silver/silverchloride reference electrode. The device was used to determine the amount of glucose in a sample to which specified and variable amounts of glucose had been added. The fiber was inserted in the test sample, and a modest vacuum was applied to the fiber lumen to induce bulk filtration flow through at approximately 6.1 microliters/minute the anisotropic membrane barrier and also to transport the filtrate to the sensor. The electrical output of the sensor was generally directly proportional to the amount of glucose in the sample, as shown by FIG. 11 in which output is plotted against glucose concentration.

The device could similarly be used to determine blood glucose in a human subject by inserting the fiber in a blood vessel. In short term experiments with human blood, an initial decay in the blood water flow rate occurred, but thereafter the rate changed very little over a period of eight hours. Thus the useful lifetime of the fibers in this respect may be many hours. Medical opinion and initial animal experiments suggest that a very thin fiber with a single insertion site could easily be tolerated in an arm blood vessel for 3-4 days and possibly for much longer periods.

Figure 12:
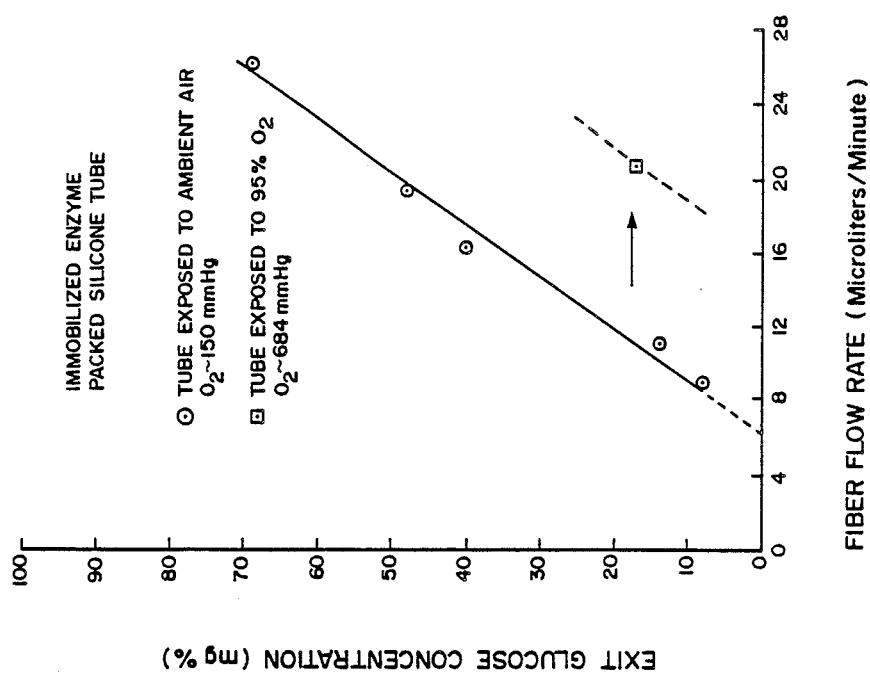
FIG. 12 is a graph showing the effect of oxygen supplied through a gas permeable silicone tube on the exit glucose concentration of filtrate fluid passing through the enzyme packed bed.

FIG. 12 is a graph showing the exit glucose concentration (mg%) of sweep fluid passing through an enzyme packed bed in an oxygen permeable Silastic tube, as utilized in Example 5, plotted against the flow rate (microliters/minute). The inlet glucose concentration was 150 mg%. Results are shown for both contacting the tube with ambient air, $O_2$ at approximately 150 mm Hg, and for providing oxygen to the tube, 95% $O_2$ for $O_2$ approximately 684 mmHg partial pressure. It can be seen that the direct supply of oxygen resulted in more complete oxidation or conversion of the glucose at a relatively high fiber filtrate flow rate, thus contributing to sensitivity of the glucose determination. However, the Example 5 results as shown in FIG. 11 indicate that results proportional to the glucose concentration can be obtained using ambient air for the glucose oxidation. Based upon these results, a fiber sensor probe having a holdup volume of 10 microliters or less will yield response times of approximately one minute or less using transmembrane pressures under approximately 200 mmHg and yielding values of the analate in the filtrate which are essentially equivalent to its level in the complex fluid.

FIGS. 13A, 13B and 13C are different microphotographic views in cross section of a polyamide anisotropic hollow fiber membrane suitable for use in the present invention. FIG. 13A shows the fiber with skin 30 on the outside and porous layer 31. The scale of this photograph is 1 mm≅10 microns. The fiber has an outer diameter ≅460 microns, inner diameter ≅420 microns, and wall thickness ≅40 microns. The outer skin layer has a thickness ≅0.8 microns. FIG. 13B is an enlarged view in section, 1.5 mm ≅10 microns, and wall thickness is ≅6 mm or 40 microns. FIG. 13C is a further enlarged view of the fiber wall in section, scale 6.5 mm ≅10 microns, showing outer skin 30 and porous section 31, with wall thickness ≅25-28 mm or 40 microns, and skin thickness ≅0.5 mm, or 0.77 micron.

FIGS. 14A, 14B, and 14C are different microphotographic views in cross section, i.e. from an end view, of a polyurethane membrane fiber suitable for use in the present invention. FIG. 14A shows the fiber has a thin outer skin, 30, and a thicker, porous supporting layer 31. The fiber has outer diameter of approximately 690 microns, inner diameter of approximately 560 microns, wall thickness (avg) of approximately 128 microns and outer skin layer (avg) of approximately 2.5 microns. The scale is 1 mm≅10 microns. FIG. 14B is an enlarged view of the fiber section, scale 1.5 mm ≅10 microns, and indicates wall thickness of 17-20 mm, or 123 microns, and outer skin of approximately 25 mm or 1.7 microns. FIG. 14C is an enlarged view of the fiber wall in section, scale 3 mm ≅10 microns, indicating wall thickness ≅40 mm, or 133 microns, and skin thickness ≅1 mm or 0.33 micron.

In the present invention it is not necessary to have a carrier gas or liquid in the fiber lumen, as liquid from the body fluid permeates into the fiber lumen and this is advantageous in regard to having concentrations comparable to those in the whole body fluid. However, in some instances it may be desirable to dilute, or add reagents to, the filtrate in the lumen for analysis, and such procedures are within the invention. The present invention is particularly useful in sampling and analysis of solid or liquid blood components, such as glucose, which may require some time for diffusion through a membrane barrier and therefore present some problems in analytical processes requiring diffusion. However, the present invention is also useful in the analysis of gaseous materials which can move through the liquid permeable barrier along with the liquid filtrate. In addition to glucose, the present invention can be used for sensing and analysis of various other body liquid components which are capable of passing through selected porous membranes.

While the present invention is particularly concerned with selective sampling of body fluid components for sensing or analytical purposes, it may also find application in the selective fractionation of body fluids with harvesting of particular fractions.

We claim:

1. A method of sampling materials in a body fluid for analysis comprising contacting the fluid with a hollow fiber of porous semipermeable asymmetric membrane with skin on the outside, of pore size permitting flow of body fluid water and desired analate to the inside of the fiber, 2nd causing such flow whereby the fluid in the inside of the fiber is essentially in instantaneous equilbrium or equivalency with the body fluid with respect to the desired analate, and the fluid in the fiber lumen is available for analysis of the analate.

2. The method of claim 1 in which the body fluid is blood.

3. The method of claim 2 in which glucose is the analate.

4. The method of claim 2 in which glucose is the analate and glucose in the filtrate is reacted in the present of glucose oxidase to form hydrogen peroxide for determination by electrical means.

5. The method of claim 2 in which the hollow fiber membrane is positioned so that it penetrates the wall of a blood vessel and it has a portion of itslength within the blood vessel.

6. The method of claim 1 in which the extra-corporeal end of the hollow fiber is within a few inches of an extra-corporeal means for sensing analate in the fiber filtrate and convective filtrate flow is directed thereto unaided by any carrier fluid.

7. The method of claim 3 in which measurement of glucose can be obtained with less than 1.0 c.c. of body fluid having been removed from the body.

8. The method of claim 1 in which analate readings are available on continuous basis.

9. The method of claim 2 in which transmembrane pressure is regulated so that fluid containing analate crosses the fiber membrane to the lumen in less than 30 seconds.

10. The method of claim 1 in which the fluid in the lumen flows to an outlet from the lumen for analysis.

11. The method of claim 2 in which glucose readings are obtained responsive to blood glucose concentrations within 30 seconds.

12. The method of claim 3 in which the filtrate in the lumen flows through a gas permeable tubing containing glucose oxidase so that glucose is reacted in the presence of excess oxygen.

13. A device for sampling and analyzing complex fluids comprising a hollow membrane fiber means for contacting such complex fluids, such hollow fiber being of porous semipermeable anisotropic membrane with skin on the outside of pore size permitting flow of complex fluid water and desired analate to the inside of the fiber, whereby liquid in the fiber lumen is essentially instantaneously in equilibrium or equivalency with the complex fluid with respect to the desired analate, and flow means connecting the fiber lumen to sensing means for determination of the analate in the liquid.

14. The device of claim 13 designed for sampling and analyzing body fluids and in which the hollow fiber membrane has porosity such as to permit passage of blood water and glucose but substantially prevents passage of materials of molecular weight over 20,000 while being permeable to materials of lower molecular weight.

15. The device of claim 13 in which the semipermeable skin of the hollow fiber has pores mainly in the range of 25 to 200 angstroms.

16. The device of claim 13 in which the hollow fiber membrane is of noningesting material with ultrafiltranteion characteristics that are stable with time.

17. The device of claim 13 in which the fiber membrane is of polyurethane or polyamide material.

18. A method of sampling materials in a complex fluid comprising contacting the complex fluid with a filtration membrane means providing bulk solvent flow and filtrate collection for analysis of complex fluid fractions, with the membrane being an asymmetric, non-ingesting mebrane with skin on the outside contacting the complex fluid.

19. The method of claim 5 in which the filtrate in the lumen flows through a gas-permeable enzyme-packed tubing for generation of hydrogen peroxide proportional to the glucose and then flows past a reference electrode and polarographic electrode generating current proportional to the hydrogen peroxide.

* * * * *